(12) United States Patent
Bienstman et al.

(10) Patent No.: US 11,475,683 B2
(45) Date of Patent: Oct. 18, 2022

(54) OBJECT CLASSIFICATION SYSTEM AND METHOD

(71) Applicants: UNIVERSITEIT GENT, Ghent (BE); IMEC VZW, Leuven (BE)

(72) Inventors: Peter Bienstman, Ghent (BE); Alessio Lugnan, Ghent (BE); Floris Laporte, Ghent (BE)

(73) Assignees: UNIVERSITEIT GENT, Ghent (BE); IMEC VZW, Leuven (BE)

( * ) Notice: Subject to any disclaimer, the term of this patent is extended or adjusted under 35 U.S.C. 154(b) by 517 days.

(21) Appl. No.: 16/616,152

(22) PCT Filed: May 26, 2018

(86) PCT No.: PCT/EP2018/063854
§ 371 (c)(1),
(2) Date: Nov. 22, 2019

(87) PCT Pub. No.: WO2018/219836
PCT Pub. Date: Dec. 6, 2018

(65) Prior Publication Data
US 2020/0125826 A1 Apr. 23, 2020

(30) Foreign Application Priority Data
May 29, 2017 (EP) ..................... 17173179

(51) Int. Cl.
*G01N 21/64* (2006.01)
*G06V 20/69* (2022.01)
(Continued)

(52) U.S. Cl.
CPC .......... *G06V 20/698* (2022.01); *G01N 21/47* (2013.01); *G01N 33/48* (2013.01); *G02B 6/1225* (2013.01);
(Continued)

(58) Field of Classification Search
CPC .. G06V 20/698; G06V 10/145; G06V 20/693; G01N 21/47; G01N 33/48; G01N 2201/06113; G01N 2201/10; G02B 6/1225; G02B 6/1228; G06N 3/0675; H04N 5/335
See application file for complete search history.

(56) References Cited

U.S. PATENT DOCUMENTS 5,812,419 A * 9/1998 Chupp ............... G01N 35/1004
  702/20
2017/0116515 A1 4/2017 Abel et al.

FOREIGN PATENT DOCUMENTS

WO 2017001438 A1 1/2017

OTHER PUBLICATIONS

Vahala, "Optical Microcavities," Nature, vol. 424, Aug. 14, 2003, pp. 839-846.
(Continued)

*Primary Examiner* — Kiho Kim
(74) *Attorney, Agent, or Firm* — Workman Nydegger

(57) ABSTRACT

An object classification system for classifying objects is described. The system comprises an imaging region adapted for irradiating an object of interest, an arrayed detector, and a mixing unit configured for mixing the irradiation stemming from the object of interest by reflecting or scattering on average at least three times the irradiation after its interaction with the object of interest and prior to said detection.

20 Claims, 15 Drawing Sheets

(51) Int. Cl.
  *G01N 21/47* (2006.01)
  *G01N 33/48* (2006.01)
  *H04N 5/335* (2011.01)
  *G02B 6/122* (2006.01)
  *G06N 3/067* (2006.01)
  *G06V 10/145* (2022.01)

(52) U.S. Cl.
  CPC ......... *G02B 6/1228* (2013.01); *G06N 3/0675* (2013.01); *G06V 10/145* (2022.01); *G06V 20/693* (2022.01); *H04N 5/335* (2013.01); *G01N 2201/06113* (2013.01); *G01N 2201/10* (2013.01)

(56) References Cited

OTHER PUBLICATIONS

Xu et al., "Pillar-Array Based Optical Sensor," Optics Express, vol. 18, No. 6, Mar. 15, 2010, 6 Pages.

Mesaritakis et al., "Micro Ring Resonators as Building Blocks for an All-Optical High-Speed Reservoir-Computing Bit-Pattern-Recognition System," Journal of the Optical Society of America—B, vol. 30, No. 11, Nov. 2013, pp. 3048-3055.

Vandoorne et al., "Experimental Demonstration of Reservoir Computing on a Silicon Photonics Chip," Nature Communications, vol. 5, Issue 3541, Mar. 24, 2014, pp. 1-6.

Zhang et al., "Integrated Photonic Reservoir Computing Based on Hierarchical Time-Multiplexing Structure," Optics Express, vol. 22, No. 25, Dec. 15, 2014, 15 Pages.

Lugnan et al., "Integrated Pillar Scatterers for Speeding up Classification of Cell Holograms," Optics Express, vol. 25, No. 24, Nov. 27, 2017, 13 Pages.

Van Der Sande, "Advances in Photonic Reservoir Computing," De Gruyter: Nanophotonics, vol. 6, No. 3, 2017, pp. 561-576.

Katumba et al., "Neuromorphic Computing Based on Silicon Photonics and Reservoir Computing," IEEE Journal of Selected Topics in Quantum Electronics, vol. 24, No. 6, Nov./Dec. 2018, 10 Pages.

European Search Report from EP Application No. EP17173179, Nov. 28, 2017.

International Search Report and Written Opinion from PCT Application No. PCT/EP2018/063854, dated Aug. 10, 2018.

\* cited by examiner

OBJECT CLASSIFICATION SYSTEM AND METHOD

FIELD OF THE INVENTION

The invention relates to the field of optical wave-based computing. More specifically it relates to methods and systems for optical wave-based computing with low loss using a mixing unit.

BACKGROUND OF THE INVENTION

The more we get swamped by Big Data, the more we let computers take over the data processing. Machine Learning is therefore currently one of the fastest growing disciplines in computer science and statistics. However, most of this processing still happens in software on power-hungry computers.

An alternative hardware implementation is a so-called Reservoir Computer specifically designed for efficient optical computation. Reservoir Computing is a machine learning branch focusing on processing of time-dependent data. It was first proposed in the early 2000s as a way of using an untrained neural network with internal feedback combined with a trained linear readout layer to perform classification of temporal data. The feedback through the nonlinear nodes in the so-called recurrent network performs a nonlinear mixing of the signal and provides a fading memory to the system.

A passive photonic reservoir computer based on the same reservoir computing principle was already proposed in 2014 by Kristof Vandoorne et al. in Nature communications 5 (2014). However, the proposed implementation suffers from fundamental scaling limits coming from the 3 dB loss associated with the sequence of combiners used in the system.

Passive photonic reservoirs may be used for a variety of applications. Nevertheless, the complexity of tasks the reservoir can perform depends on the number of neurons it consists of, these losses also limit the complexity of tasks that can be performed, and consequently there is still room for improvement.

SUMMARY OF THE INVENTION

It is an object of embodiments of the present invention to provide efficient passive photonic wave-based computing methods and systems based on a mixing unit which show low losses.

The present invention relates to an object classification system for classifying objects, the object classification system comprising an imaging region adapted for irradiating an object of interest, an arrayed detector, and a mixing unit configured for mixing the irradiation stemming from the object of interest by reflecting or scattering on average at least three times the irradiation after its interaction with the object of interest and prior to said detection. The mixing unit may be configured for reflecting or scattering on average at least five times, e.g. on average at least ten times the irradiation after its interaction with the object of interest. The mixing unit may comprise a plurality of scatterers. Alternatively, the mixing unit also may be a cavity with reflective walls comprising an input and a plurality of outputs. Examples thereof are also described further.

Where in embodiments of the present invention reference is made to "complex scattering or reflection" or to "on average at least N times the irradiation is scattered or reflected" this may include that on average at least N different portions of the irradiation can be scattered or reflected in different ways (i.e. spatially) and/or that on average a same portion of the irradiation is scattered or reflected at least N times (i.e. temporally). N thereby may be a large number, such as for example 3, 5 or 10. For the spatial reflections, this includes situations where a portion of the irradiation is reflected or scattered only once or even never by the mixing unit. In other words, this may include the situation wherein a lot of different parts of the radiation coming from the object are reflected or scattered in different ways. Alternatively, this may be formulated as at least once a significant part of the irradiation is reflected or scattered, whereby a significant part may be at least one fifth of the total light forward scattered by the object. When in a particular embodiment scatterers are placed in layers, the complex scattering or reflecting condition or the condition that on average at least N times the irradiation is scattered or reflected, this thus includes an embodiment wherein a single layer of scatterers is used, whereby at different spatial positions the radiation will be scattered differently at different positions.

The system further may comprise a classifier for classifying the objects based on the irradiation obtained after said mixing. The classifier may be a linear classifier or may be a more complex classifier, such as for example a feedforward neural network.

The arrayed detector may be a line scan image sensor.

The linear classifier may be implemented in the electrical field, receiving input signals from the line scan image sensor.

The linear classifier may be based on a weighted sum of the input signals.

The mixing unit may comprise a random set of scattering objects.

The scattering objects may be scattering pillars.

The random set of scattering objects may be positioned in a cavity. The scattering objects may be arranged in a plurality of layers, each layer comprising a row of randomly positioned scattering objects.

The mixing unit may comprise a cavity which may be formed from silicon nitride and the scattering pillars being made of silica.

The mixing unit may be a photonic crystal cavity.

The mixing unit may be a cavity made in silicon, whereby ferroelectric thin films are coated on the cavity.

The mixing unit may be a photonic crystal cavity made of silicon rods wherein in the middle nonlinear polymers are introduced.

The mixing unit may comprise a cavity being made in a III-V material.

The system may comprise a plurality of mixing units coupled in a hierarchical arrangement.

The mixing units being coupled in a hierarchical arrangement may comprise a first mixing unit taking care of lower-level features in the input signal and further mixing units for taking care of higher-level features.

The imaging region adapted for irradiating an object of interest may comprise a microfluidic channel for carrying the object in a fluid.

The system may be a cell classification system.

The present invention also relates to the use of an object classification system for classifying cells.

The present invention further relates to a method for classifying objects, the method comprising irradiating an object of interest, mixing the irradiation after interacting with the object of interest and prior to the detection of the irradiation in the detector by reflecting or scattering on average at least three times using a mixing unit, and detecting the mixed irradiation with an arrayed detector. The method may comprise applying a linear classification of the detected mixed irradiation.

The mixing may comprise mixing a static, non-time dependent irradiation signal, detecting said mixed signal and deriving therefrom a classification for the object of interest.

The present invention relates to a passive photonics wave-based computing system configured for performing wave-based computing, the system comprising a mixing unit comprising at least one input and a plurality of outputs, the mixing unit further being configured for reflecting or scattering in a complex way of an optical beam received via said at least one input towards at least one of said plurality of outputs. The mixing element may be a photonic crystal cavity or may be a scattering based mixing unit. It is to be noted that the mixing unit typically may be substantially larger than the wavelength or than the order of the wavelength. The mixing unit may be at least larger than 5 times the wavelength with which the system will be used.

The at least one input may be a plurality of inputs. The mixing unit has a plurality of outputs. Such outputs may be combined, e.g. using weighing and summing, such that the overall wave-based computing system may only have a single output.

It is an advantage of embodiments of the present invention that the mixing unit allows to provide good mixing of input radiation, without large losses occurring. The latter is obtained by avoiding at least some combiners and splitters in the system and instead using a mixing unit.

Where in embodiments of the present invention reference is made to a cavity, reference is made to a region in the photonics device, that is typically filled with transparent materials, being transparent for the wavelengths of the radiation for which the system can be used and that comprises reflective elements at the edge, e.g. reflective walls.

The mixing unit may be configured in the passive photonics wave-based computing system so that it acts as a fading memory for the radiation signals.

The mixing unit may be a cavity comprising a plurality of reflective walls such that after a plurality of reflections radiation from the inputs eventually will reach an output port.

The mixing unit may be a photonic crystal cavity.

The mixing unit may have a shape of a quarter-stadium.

The input and/or output waveguides may be connected to the mixing unit through adiabatic tapers.

The mixing unit may be a cavity made in silicon, whereby ferroelectric thin films are coated on the cavity, wherein the mixing unit is a photonic crystal cavity made of silicon rods wherein in the middle nonlinear polymers are introduced, or wherein the cavity is made in a III-V material.

The system may comprise a plurality of mixing units coupled in a hierarchical arrangement.

The mixing units being coupled in a hierarchical arrangement may for example comprise a first mixing unit taking care of lower-level features in the input signal and the further cavity(ies) for taking care of higher-level features.

The mixing unit may comprise a random set of scattering objects.

The scattering objects may be scattering pillars.

The random set of scattering objects may be positioned in a cavity.

The cavity may be formed from silicon nitride and the scattering pillars may be made of silica.

The present invention also relates to a method for performing photonic wave-based computing, the method comprising applying an optical input signal to one or more inputs of a mixing unit, allowing the optical signal to propagate in the mixing unit, said propagating comprising complicated reflecting or scattering of said optical signal received via said at least one input towards at least one of a plurality of outputs, and thus obtaining a nonlinear readout in at least one of said plurality of outputs. The nonlinear readout is obtained after being detected by the detector. In at least some embodiments of the present invention, the method performed is strictly speaking not a traditional reservoir computing technique but rather a sort of spatial variant of the concept, since the inputs, are static. In embodiments of the present invention, typically no time-dependent signals are used.

The method furthermore may comprise sampling the signals at discrete time intervals to combine the signals in a single output signal.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
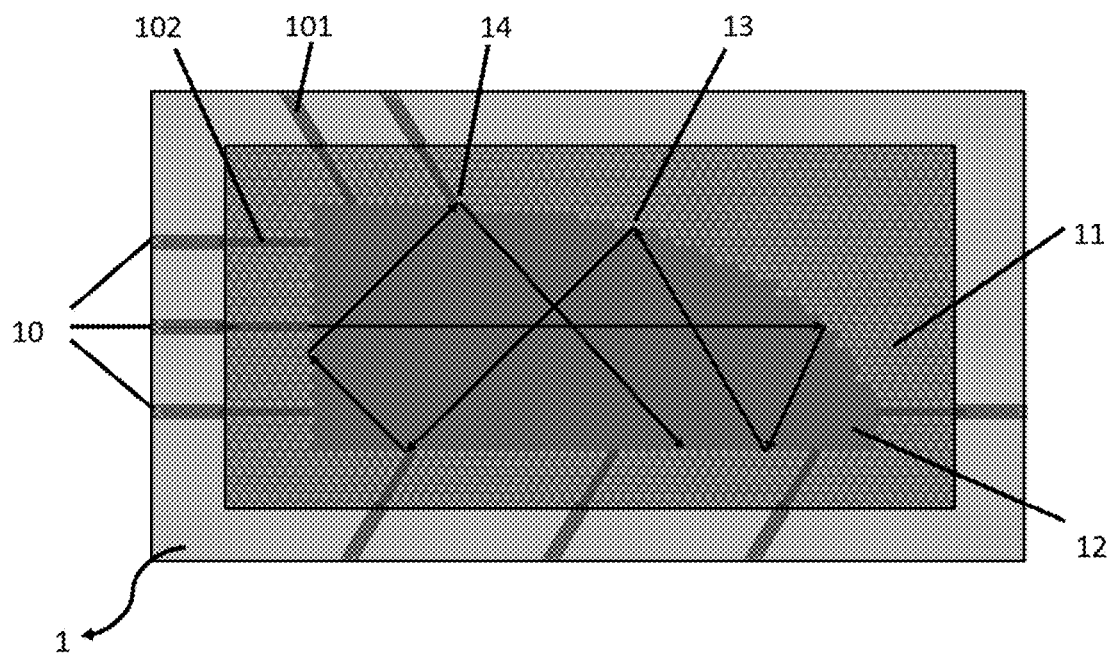
FIG. 1 illustrates a mixing unit comprising a photonic crystal cavity with a plurality of input and output connectors, according to an embodiment of the present invention.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect the present invention relates to an object classification system for classifying objects, the object classification system comprising an imaging region adapted for irradiating an object of interest, an arrayed detector and a mixing unit configured for mixing the irradiation stemming from the object of interest by reflecting or scattering on average at least three times the irradiation after its interaction with the object of interest and prior to said detection. This may mean that at least three portions of the irradiation may be reflected in a different way and/or that a same portion of the irradiation may be subsequently reflected three times. In some embodiments, the object classification system advantageously also comprises a classifier for classifying the objects based on the irradiation obtained after said mixing. The classifier may be a linear classifier or a more complex classifier. Further in the description, by way of illustration, an exemplary object classification system will be described and simulated, thus showing standard and optional features and advantages of the object classification systems according to embodiments of the present invention. The type of mixing unit may be based on scatterers and/or may be based on a cavity with reflective walls. Such mixing units may correspond with mixing units as disclosed for the passive photonics wave-based computing systems described in the further aspects of the present description. Features and advantages may be applied to the object classification system mutates mutandis.

In one aspect the present invention also relates to the use of an object classification system for classifying objects, such as for example cells. In some embodiments, the object classification system may be applied for performing distinguishing between healthy cells and non-healthy cells, such as for example cancerous cells. Nevertheless, embodiments are not limited thereto and other applications also are envisaged, such as for example classification or detection of different types of biological cells (e.g. blood cells), different types of microparticles (also of non-organic nature), different types of flowing fluids, distinguishing between particles of different sizes and/or different composition, etc.

In another aspect, the present invention relates to a method for classifying objects, the method comprising irradiating an object of interest, mixing the irradiation after interacting with the object of interest by reflecting or scattering at least three times using a mixing unit, and detecting the mixed irradiation with an arrayed detector. This may mean that at least three portions of the irradiation may be reflected in a different way and/or that a same portion of the irradiation may be subsequently reflected three times. The mixing may comprise mixing a static, non-time dependent irradiation signal, detecting said mixed signal and deriving therefrom a classification for the object of interest. The method also may comprise applying a classification, e.g. linear or more complex, of the detected mixed irradiation. More generally, the method also may comprise applying non-linear postprocessing. Further method steps may correspond with the functionality of the features of the device aspects described in this description.

In still another aspect the present invention relates to a passive photonics wave-based computing system configured for performing wave-based computing. The wave-based computing has similarities with reservoir computing. Nevertheless, use may be made of time independent signals whereas for reservoir computing typically time dependent signals are used. According to embodiments of the present invention, the system comprises a mixing unit having at least one input and a plurality of outputs. It is to be noted that whereas the mixing unit typically has a plurality of outputs, the overall wave-based computing system may have a single output, whereby e.g. the single output of the overall system is obtained by combining, e.g. summing, weighted signals from the outputs of the mixing unit. The mixing unit furthermore is configured for complicated reflecting or scattering of an optical signal received via said at least one input towards at least one of said plurality of outputs. The wave-based computing system may be implemented in a plurality of ways. Two particular implementations will be described, one implementation whereby the mixing unit is based on a photonic crystal cavity comprising reflective walls for reflecting in a complex way an optical signal received via at least one input and a second implementation whereby the mixing is based on a plurality of scattering elements, e.g. pillars. Examples of both types of implementations will be described below, embodiments not being limited thereto. The wave-based computing system may, besides a mixing unit comprising at least one input and a plurality of outputs also comprise a readout layer for processing the output of the mixing unit, as well as a further output for outputting a result of the system. The computing system may comprise a non-linearity. The computing system also may comprise a static memory, implemented optically or in a hybrid opto-electronic way.

By way of illustration, an embodiment wherein the mixing unit is based on a photonic crystal cavity comprising reflective walls for reflecting in a complex way an optical signal so as to mix it will further be described with reference to FIG. 1 which shows a schematic drawing of a mixing unit comprising a photonic crystal based cavity together with a plurality of input and output connectors.

A cavity 12 is designed and optimized as the mixing unit 1 of the passive photonics wave-based computing system so that good mixing of the inputs is achieved, e.g. through an effective randomization of the propagating wave direction inside the cavity 12 after a large number of reflections 13. The cavity shape typically displays curved features, for example the arc of a quarter-stadium cavity, but many other cavity shapes may be considered as mixing unit too. In a particular example, a quarter-stadium design may display 30 μm and 15 μm long semi-axis, however these numbers can vary according to a particular task to be solved and the required speed of the input signals. It is an advantage of the present invention to show low losses under the mixing procedure which is achieved by the multiple reflections 13 off the reflective cavity walls 11 before being partially transferred into one or more outputs 14. High reflectivity from the enclosing boundary 11 walls of the cavity may be obtained by the use of a photonic crystal structure comprising a regular lattice of air holes in silicon, but is not limited thereto and other material interfaces of the cavity walls may be conceived. Propagation losses, scattering losses, surface losses, and other sources of imperfections in the material and fabrication are typically small compared to the coupling losses induced by the plurality of input and output ports 10 connected to the cavity. Hence the number of input and output connectors 10 constitutes the major control variable of the cavity's quality factor (Q-factor). The Q-factor is related to the lifetime of a cavity 12 excitation through one or more of its input connectors 10; the final decay of any excitation through loss mechanisms provides a form of fading memory to the passive photonic computing system. A reasonable minimum number of input and output connectors to perform computational tasks with low error rates is typically ranging between five and nine, corresponding to Q-factors between 3000 and 5000, but different choices may lead to better results in some cases. A higher Q-factor can be obtained by reducing the number of input and output connectors which gives rise to better system memory but trades system bandwidth.

It is of advantage of the described embodiment that the input connectors 10 can serve as output connectors at the same time, thus limiting the complexity of the overall system. Furthermore, the input or output connectors 10 typically comprise of an adiabatically controlled taper 101 connecting to the external input or output waveguides and a defect waveguide 102 inside the photonic crystal structure, both ensuring that input and output radiation signals are delivered to and coupled out from the cavity 12. The tapered sections 101 can be tailored to inject or extract a given fraction of the incident radiation signal, hence are another means to control the cavity's Q-factor. Typical transmissivity values range from 30% to 95%, but can be adapted accordingly and on an individual basis. Moreover it is possible, although not required to add delay lines to the input or output connectors 10 in order to provide for increased memory and better signal mixing properties of the mixing unit 1.

Furthermore, an embodiment of the present invention may benefit from the flat surface structure of the cavity 12 which is ideally suited for deposition of thin film coatings, e.g. ferroelectric thin films but not limited thereto. In a likely manner, a cavity region 12 based on air surrounded by photonic crystal walls made from silicon rods is an embodiment of the present invention that could be filled with a nonlinear material, nonlinear polymers for instance. Another possibility is to pattern the cavity 12 into a III-IV material. All the mentioned optional features provide an enhanced nonlinear response to the mixing unit 1 which may lead to increased efficiency or computational power of the passive photonic computing system.

It may be an advantage of the present invention to stack several mixing 1 units together or to combine them into a hierarchical architecture which may allow for a more efficient allocation of computing resources, faster problem solving, or the treatment of derived high-level features.

By way of illustration, further features and characteristics will be described with reference to FIG. 1. The particular quarter-stadium shape shown typically shows interesting dynamics and results in complete mixing of the fields, in the sense that an input wave will obtain all possible wavevectors in the cavity. The mixing unit behaves like a fading memory necessary for wave-based computing.

With respect to its operating, in order to perform operations at a certain bitrate, the lifetime of the cavity should be a least larger than the bit period. Apart from optimising Q-factor and waveguide coupling, we can also simply increase the size of the cavity if we want to process signals with a lower bitrate. This is a valid option, since the propagation losses are small compared to the scattering and coupling losses.

Another important parameter closely related to the Q-factor of the cavity is the half life T½ of a pulse in the cavity, which is deemed as the point where the amplitude of the envelope of the field reaches half of the original amplitude. The half life is related to the Q factor as $$T_{\frac{1}{2}} = \frac{Q\log(2)}{\pi f}$$

Figure 2A:
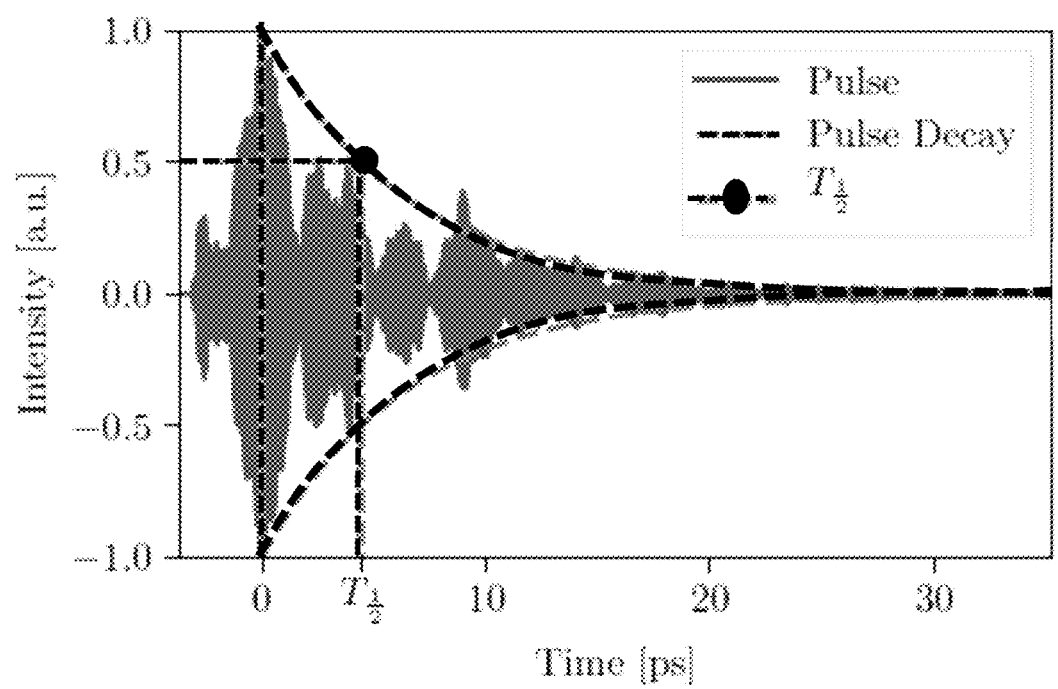
FIG. 2a and FIG. 2b illustrate the pulse decay for a cavity with 9 respectively 5 connected waveguides, according to embodiments of the present invention.
Figure 2B:
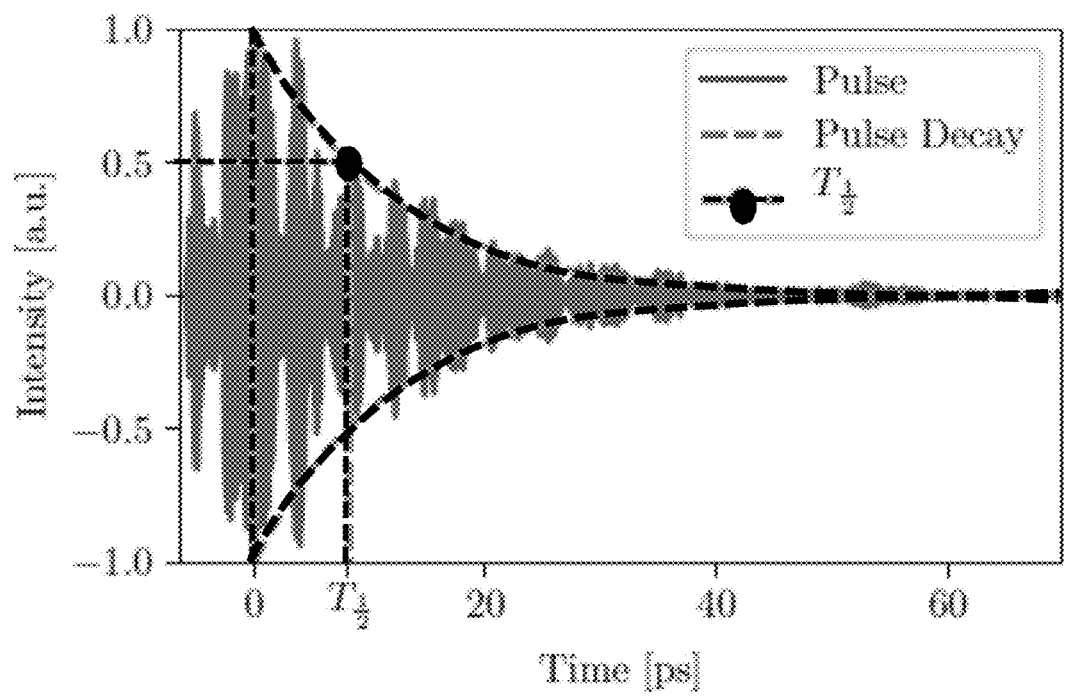
Figure 3:
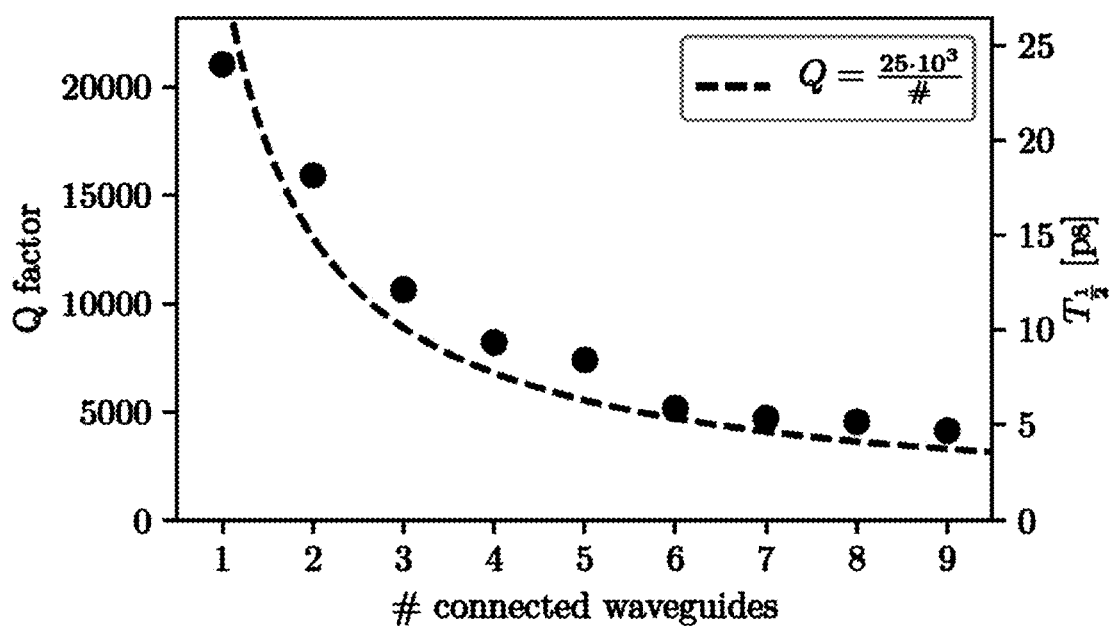
FIG. 3 illustrates the harmonical decay of the Q factor and $T_{1/2}$ with increasing number of exit waveguides, according to embodiments of the present invention.

By way of illustration FIG. 2a and FIG. 2b illustrate the pulse decay for a cavity as shown in FIG. 2 having 9 connected waveguides respectively 5 connected waveguides. The decay for a pulse having a half life of 5 ps in the cavity is shown. The half life is—just as the Q-factor—a determining factor for the memory of the system. A reduced number of connected waveguides (b) yields a higher T½ (and thus longer memory) of 8.2 ps, while more connected waveguides yield a shorter half life time T½ of 4.42 ps which will result in a shorter memory. FIG. 3 illustrates the Q factor and $T_{1/2}$ decay monotonously with increasing number of exit waveguides.

It is immediately clear that a higher pulse half life will result in a longer (fading) memory.

Therefore (as is depicted in FIG. 2b and FIG. 3), the memory can be considerably increased by reducing the number of connected waveguides. However, this reduces the number of output nodes that can be used by the readout. There will thus be a clear trade-off between the computing power of the cavity (number of exit waveguides) and the memory of the cavity (Q-factor)$^3$. The trade-off will also very much depend on the application being studied, making it difficult to give concrete guidelines. However, the Q factor should be more than 3000 in order to perform useful operations.

In some embodiments, the cladding is used for further designing the cavity. The cladding may be made of a photonic crystal, but alternatively in one example the whole cavity can in fact be made purely out of silicon with air cladding. However, to reduce losses, a photonic crystal cavity may be preferred. This design can consist out of a silicon slab with air holes or even the reverse option. The first step in designing the cavity preferably comprises optimizing the Q-factor for the desired wavelength range. This optimization can for example be done by performing several FDTD simulations for different values of the lattice constant of the photonic crystal and the radius of the photonic crystal. Next, the entrance efficiency of the entrance coupling may be optimized by optimizing an adiabatic taper where the holes of the photonic crystal are systematically introduced in an adiabatic manner.

In some embodiments, if the intensity of the light is high enough inside the cavity, the nonlinearities of silicon become more and more important. These nonlinearities can yield important extra computing power in the context of wave-based computing. To enhance these inherent nonlinearities in silicon, one could in principle deposit nonlinear thin films on top of the cavity such as the ferroelectric materials LiNbO3 or BaTiO3. Another way is to have a photonic crystal cavity made out of silicon rods, where in the middle (the air cavity) some nonlinear polymers such as rhodamine are introduced. A third option is for example to make the cavity out of known III-V materials, where the inherent nonlinearities are higher than in silicon.

In some embodiments, the signal may be inputted in more than 1 access waveguide. E.g., inputting the original input in 1 waveguide, and a suitably delayed signal in another waveguide will lead to better mixing.

In some embodiments, as a possible solution for the memory-outputs trade-off, use is made of multiple coupled photonic crystal cavities in a hierarchy, whereby the first cavity takes care of lower-level features in the input signal, and the next cavities take care of higher-level features. Alternatively, when needing to detect an 8 bit pattern e.g., there could be one cavity to recognise the first 4 bits, and a second cavity with a suitable delay to detect the last 4 bits. This information could then be combined in a higher-level readout layer in order to detect the full 8 bits.

Figure 5:
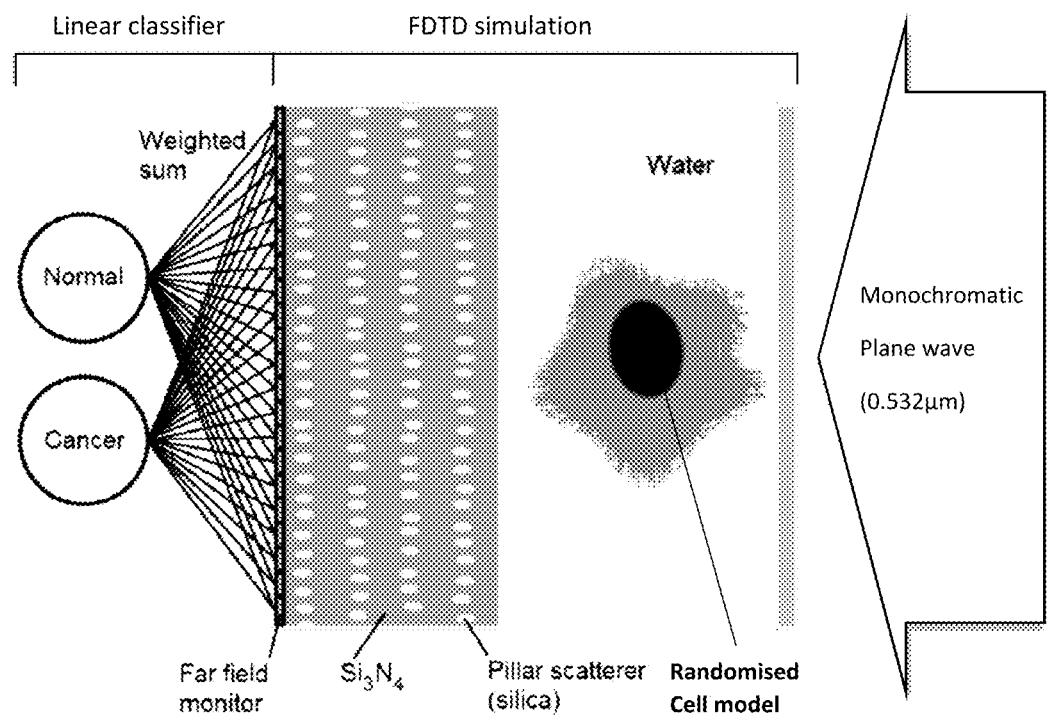
FIG. 5 illustrates a mixing unit comprising a plurality of scatterers according to an embodiment of the present invention.

Also by way of illustration, an embodiment wherein the mixing unit of the wave-based computing system is based on a plurality of scatterers, optionally in a cavity, is further discussed. An example thereof is shown in FIG. 5, in the present example being suitable for identification of types of cells (e.g. cancer cells) and more particularly by direct processing of a hologram using wave-based computing, although the invention is not limited thereto and also other types of characterization can be performed.

The scatterer configuration of the plurality of scatterers has a large number of degrees of freedom and its complete exploration, even using smart methods as evolutionary algorithms, would be computationally quite expensive. In fact, for each tested configuration, hundreds or thousands of simulations have to be performed in order to provide the classifier with a sufficient number of training and test samples. Therefore, only a few general parameters that control the complexity of the collected interference pattern were explored, looking for a maximum in the classifier performances. In the present example, the scatterers are placed in layers, e.g. vertical layers as shown in FIG. 5 with an average vertical distance between their centers of 1 µm. The center of each scatterer is randomly displaced with respect to their unperturbed center in the layer, both along the vertical and the horizontal directions. All the random displacements are sampled from the same uniform probability distribution. The considered parameters for the structure optimization are:

the amplitude $A_{rand}$ of the scatterers' random displacement;

the horizontal distance D between the layers;

the number $N_{layers}$ of layers.

Figure 6A:
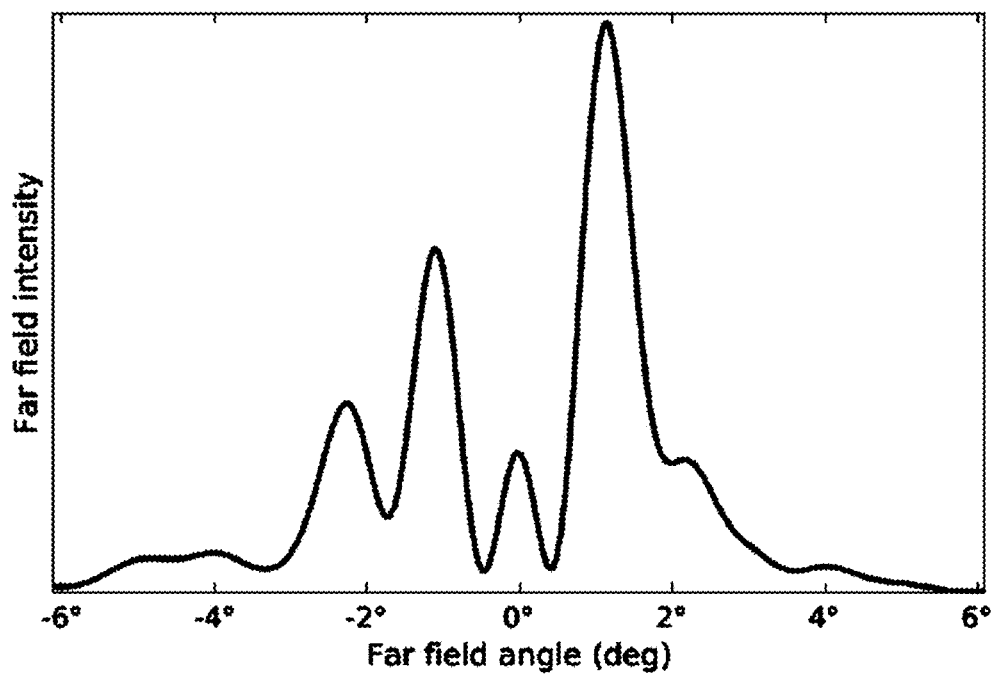
FIGS. 6a to 6c illustrates the effect of scatterers on an incoming radiation signal, according to an exemplary embodiment of the present invention.
Figure 6B:
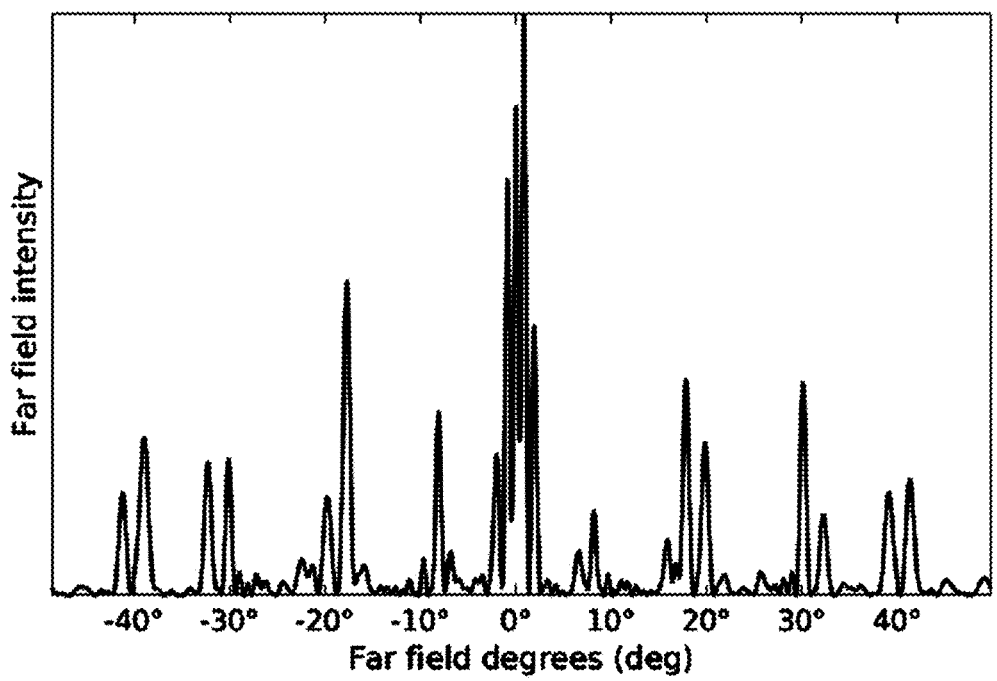
Figure 6C:
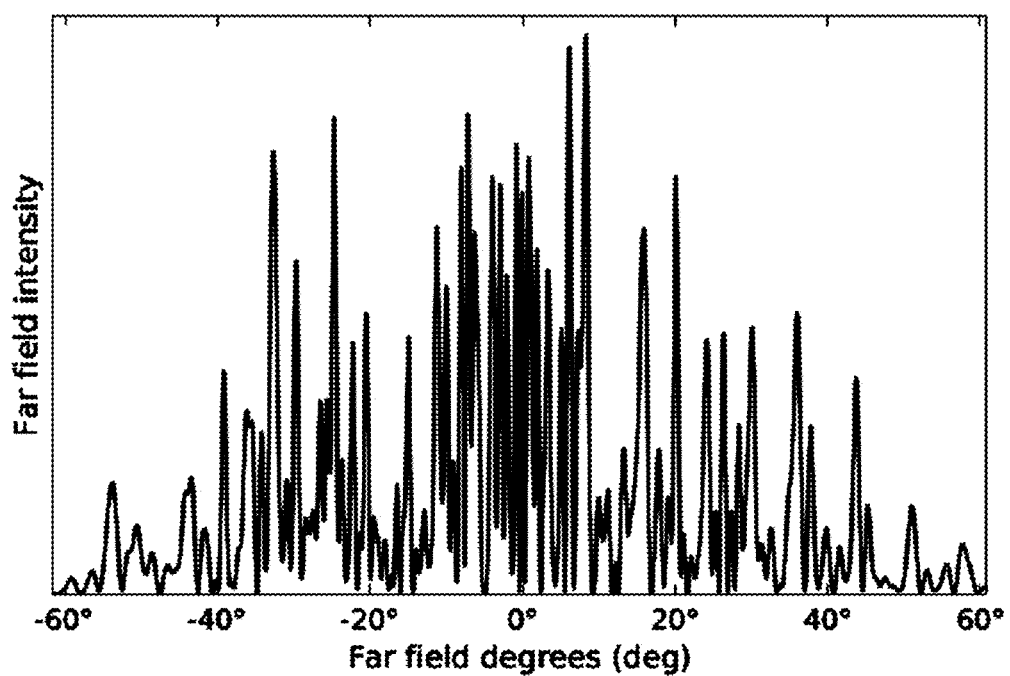

An example of how these parameters can modify the interference pattern is given in FIGS. 6a, 6b and 6c. FIG. 6a illustrates the situation without scatterers, FIG. 6b illustrates the situation with 4 layers of scatterers without random displacement and FIG. 6c illustrates the situation of 4 layers of scatterers with random displacement. It can be seen that for this particular incarnation, the interference pattern in case no scatterers are present is relatively simple and smooth and confined between −6° and 6°, that the interference pattern in case of 4 layers of scatterers without random displacement shows peaks only in bounded angle regions between −50° and 50° and that the interference pattern in case of 4 layers of randomly positioned scatterers is complicated and shows intensity peaks between −60° and 60°.

In another aspect, the present invention provides a method for performing computation on the wave-based photonic system.

Figure 4:
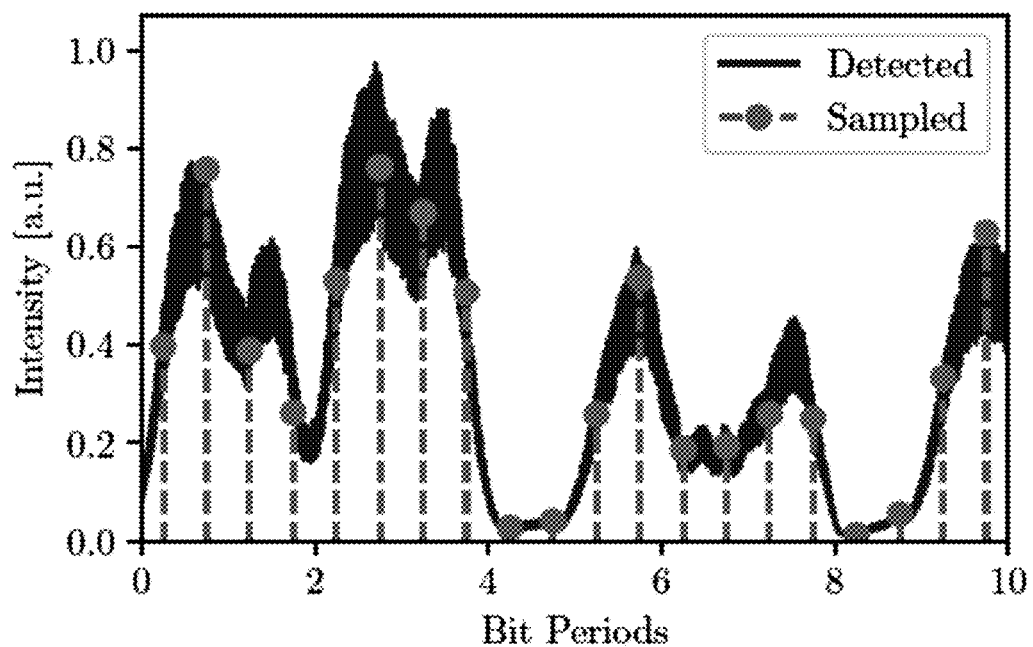
FIG. 4 illustrates sampling of the detected signal at discrete time intervals according to embodiments of the present invention.

The method according to embodiments comprises applying an input to one or several of the connected inputs, e.g. input cavity waveguides. In a following step, the signal then propagates through the mixing unit and mixes in a complicated and possibly non-linear manner. The mixing of the original signal happens in a passive way, until the signal is outputted. For the outputting, a quadratic nonlinearity may be applied the complex signal consisting of an amplitude and phase may result in a real-valued magnitude of the signal. This typically happens when reading out with a photodiode. After the readout step, the readout signal may in some examples be sampled at discrete time intervals to be combined into a single output signal using pretrained weights. The sampling is shown in FIG. 4.

By way of illustration, a particular embodiment based on a mixing unit comprising a photonics waveguide cavity will be described below. The exemplary method comprises the following steps described hereafter, but modifications and extensions to the said steps are not excluded.

One or more input signals are injected into the body of the cavity 12 making use of the adiabatically tapers 101 and defect waveguides 102 of the input connectors 10. The input signals are typically guided, time-encoded, modulated photonic waves that were coupled into the signal carrying waveguides surrounding the mixing unit 1 and terminating at the input connectors 10. Each of the input signals injected into the cavity 12 undergoes a long sequence of reflections 13 off the cavity walls 11, spreading at the same time by the phenomena of diffraction of the aperture at the end of the defect waveguides 102. The reflections 13 and propagation of the excited waves inside the cavity 12 are typically nearly lossless. During the propagation inside the cavity 12, the excited waves encounter 14 pierced sections of the cavity wall, the output connectors 10, the purpose of which is to couple out a fraction of the light wave incident on that connector. The outcoupled waves from the cavity 12 are then routed to a detecting unit, e.g. an integrated photodetector module, which applies a nonlinear readout transformation. Typically this occurs to be the conversion of photonic guided signals in the complex domain to their electronic counterpart in the real domain only; the nonlinear transformation being the square modulus translating electric field strengths into corresponding optical power values. In a subsequent step, the nonlinearly transformed signal may be sampled at regular time intervals and combined into a single output signal by a linear weighting function.

In one aspect, the present invention also relates to a method wherein the mixing step is performed by scattering using a plurality of scattering elements, e.g. pillars. The output of the mixed signal may then be lead to a detection unit where the output signal may be evaluated.

Example 1

In the first example, benchmarking of the wave-based computing system as shown in FIG. 1 is discussed.

Figure 7:
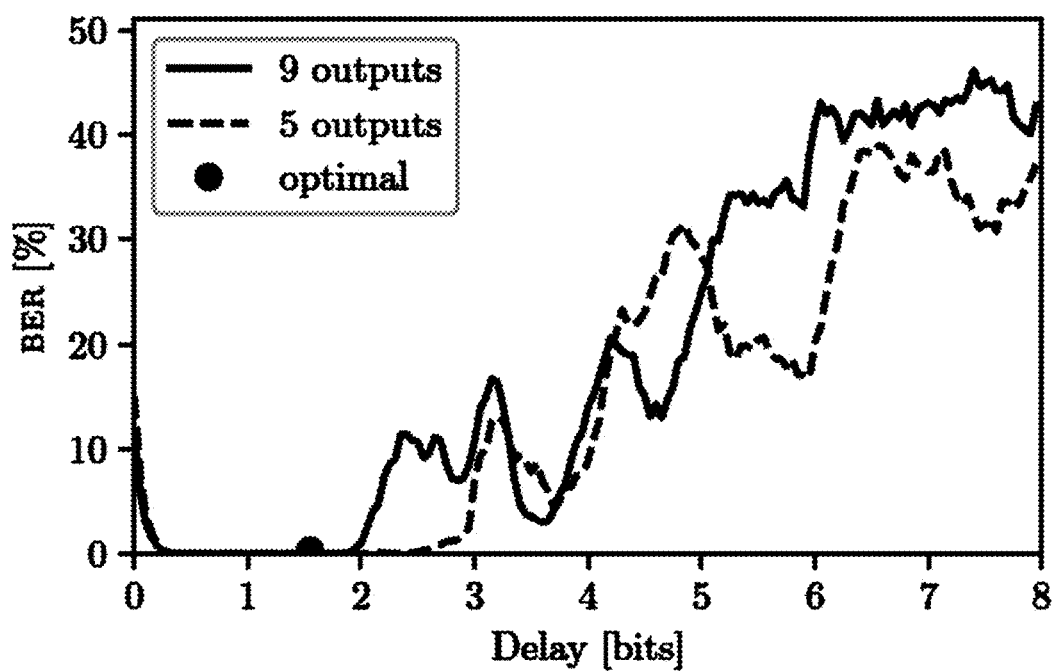
FIG. 7 illustrates the BER as function of the delay.

A first benchmark for the memory of the signal is the ability to reproduce the exact input with a certain amount of delay. From FIG. 7, for the current design, there is quite a wide basin of operation. Using 5 outputs results in being able to reproduce the input with a larger delay, which makes sense because of the increased Q factor and thus memory for 5 outputs.

A second benchmark which illustrates the ability to perform Boolean operations is the nonlinear xor task, where the xor is taken between two bits $b^n$ and $b^{n-k}$, k bits apart. Since a normal conventional linear classifier can only achieve a minimum of 25% error rate, it is also a good performance indicator of the nonlinearity in the system.

Figure 8A:
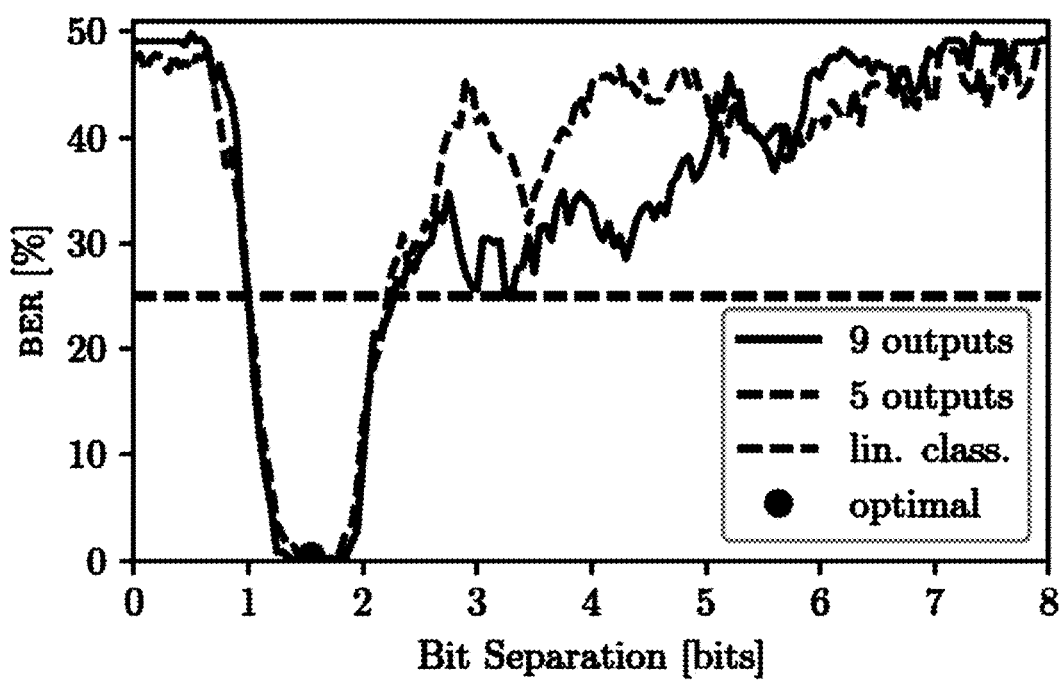
FIG. 8a describes the error for 9 connected waveguides vs. 5 connected waveguides.
Figure 8B:
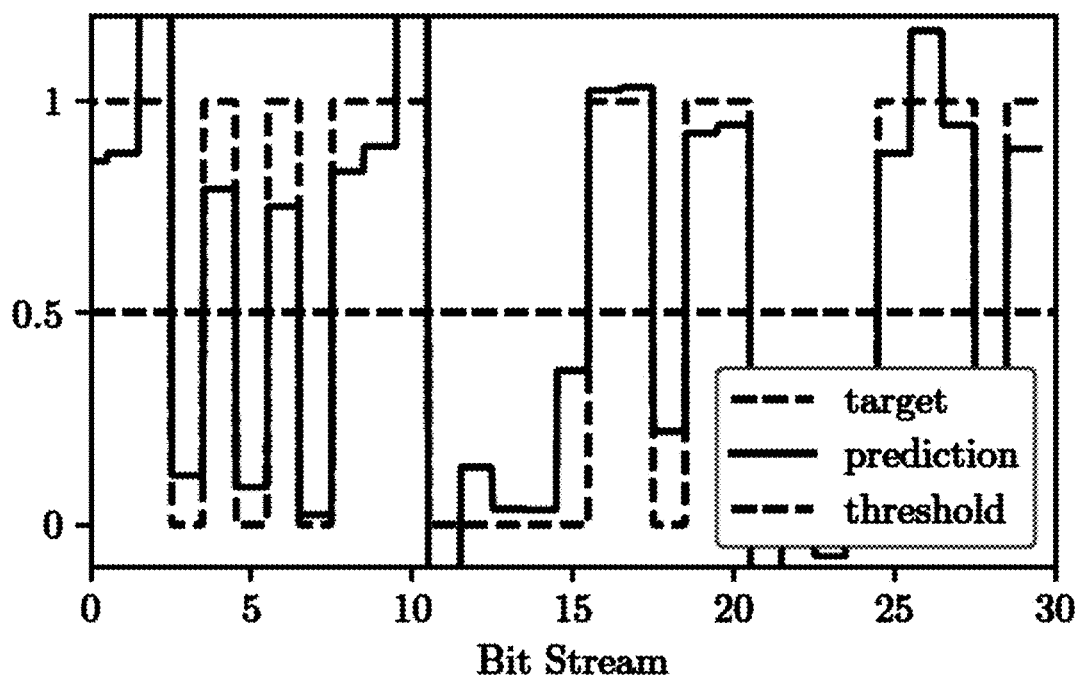
FIG. 8b describes the target and predicted bit stream at 100 Gps and for the optimal delay (1.55 bit periods) for a SNR=3.

First, the performance of an xor on two neighboring bits was assessed, while continuously increasing the bit separation. We call this the xor-specific memory of the reservoir, as it is an indicator of how good the wave-based computing system can remember the combined xor of two bits. As can be seen in FIGS. 8a and 8b, the performance is clearly worse than the delay memory.

Contrary to the linear memory task, the performance of the wave-based computing system does not really depend on the number of waveguides that is being used as input waveguides, as can be seen in FIGS. 8a and 8b.

This is probably because the performance in this case is determined limited by the nonlinear character of the task, and not so much by the linear memory capacity.

In fact, the most important figure to classify the performance of the reservoir, is probably the bitrate at which it operates optimally. The performance of the wave-based computing system for the xor operation between neighboring bits $b^n \text{xor} b^{n-1}$. This operation is optimal at 45 Gbps for the wave-based computing system with 9 connected waveguides. This bitrate may seem high, but this optimal bitrate can be easily reduced by creating a bigger cavity. Therefore we also choose to quantify the optimal performance by the dimensionless parameter T½/Tbit. This allows us to easily scale the wave-based computing system operating range by tweaking its design parameters.

Figure 9A:
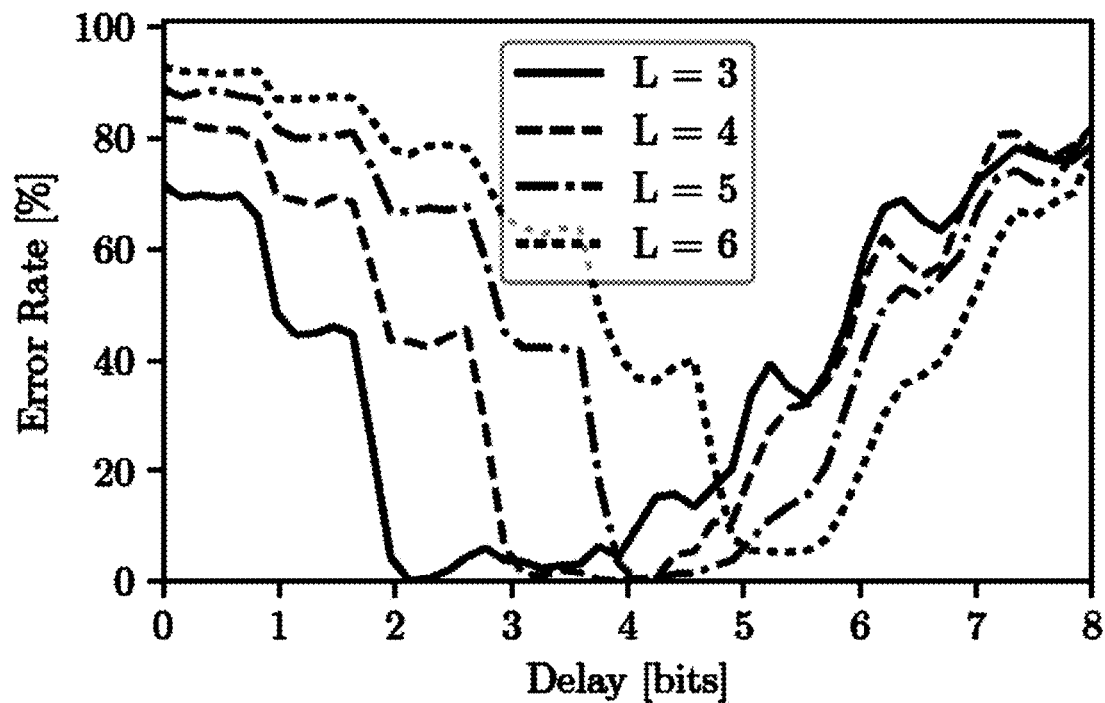
FIG. 9a illustrates that the wave-based computing system can distinguish up to 4 bits without error and FIG. 9b illustrates that for a header of length of 5 bits, the average error rate per header is still well below 5%, illustrating advantages of embodiments of the present invention.
Figure 9B:
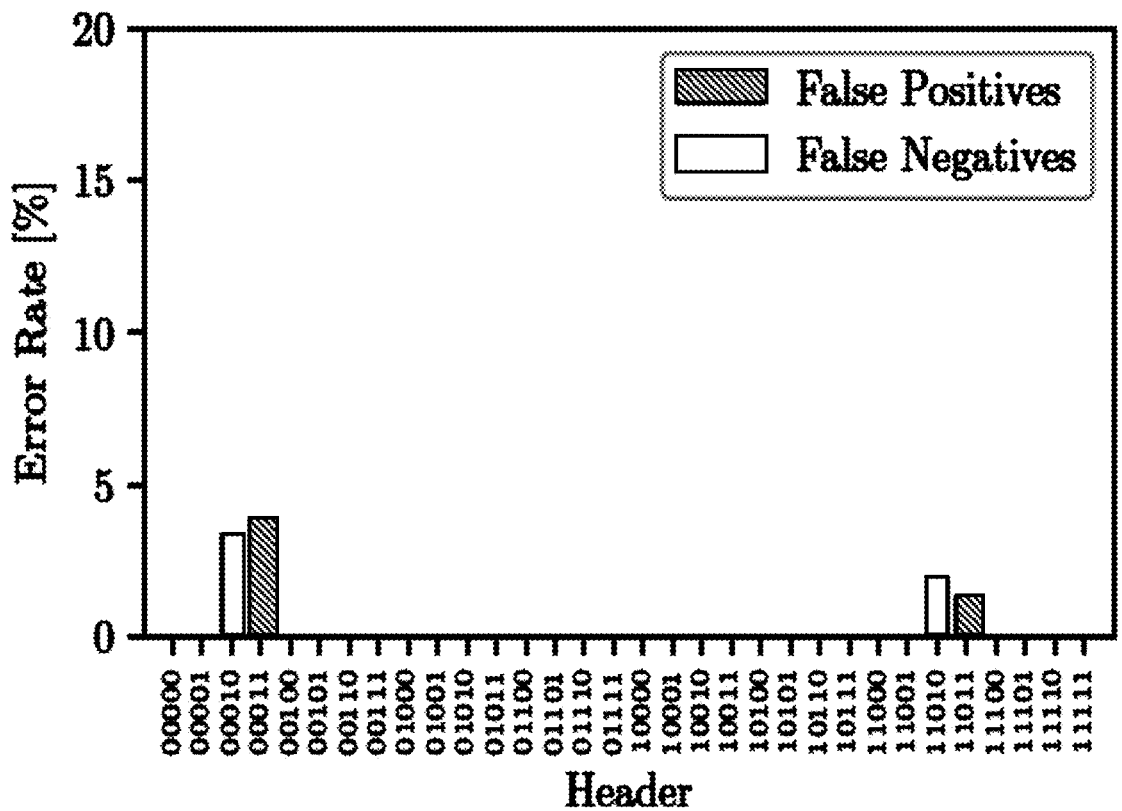
Figure 10:
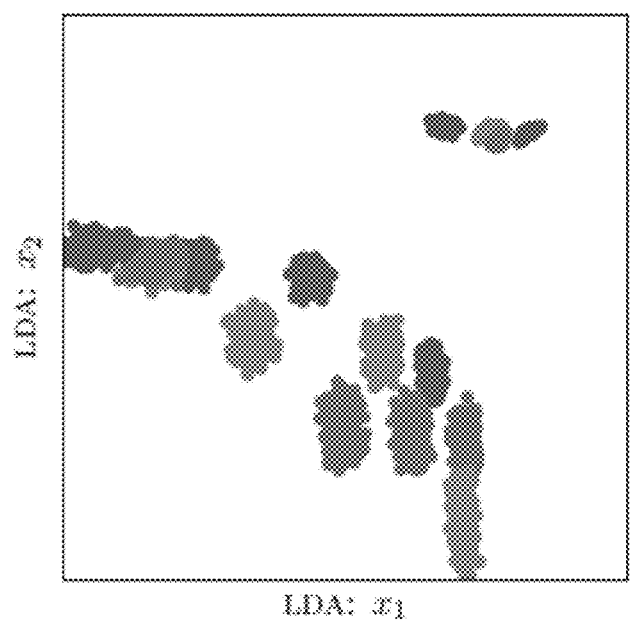
FIG. 10 illustrates a Linear Discriminant Analysis used to discern different headers, as can be used in embodiments of the present invention.

As a more useful and general task, the performance of the wave-based computing system in recognizing headers in a bitstream was assessed. The simple cavity performs reasonably well for header recognition tasks, with an errorless recognition of up to 4 bit headers 5, while very good performance for 5 bits headers is also achievable. Note that performance for a higher number of bits can be improved by a cascaded system, as mentioned above, by training each of the cascaded systems for a different subset of the header. In this case, Linear Discriminant Analysis was used as the linear classification algorithm. This algorithm allows us to project the 9-dimensional (#connected waveguides) output state to a lower dimensional state, as is shown in FIG. 9a, FIG. 9b and FIG. 10.

Example 2

In the second example, the simple passive photonic chip containing a collection of silica pillar scatterers embedded in silicon nitride as shown in FIG. 5 is used as interface between a biological cell hologram projection and a line-scan image sensor, in order to simplify and speed up a machine learning processing on the acquired image. In particular, the classification of cells of different nucleus sizes flowing along a microfluidic channel equipped with a digital holographic microscope was simulated through 2D FDTD simulations. The scatterers are employed to better exploit the nonlinear relation that links the cell refractive index structure (and the corresponding phase shift exerted on the impinging light) with the radiation intensity collected by the sensor. In this way, the complexity of a nonlinear stage can be controlled in order to increase the performances of a linear classifier that acts on the output of the sensor pixels. The proposed implementation illustrates that embodiments of the present invention employ the same principles of the well-known wave-based computing technique for time-dependent signals and applies them on spatial-dependent signals. It will be shown that the exact geometric details of the scatterers seems to be less relevant to achieve good performance. The wavelength of the light used however should result in sufficient optical path length difference for the different cases to be distinguished.

By way of illustration, results of the use of a passive wave-based system for detection of cells, as shown in FIG. 5 will further be described.

The process was studied via 2D FDTD simulations as a proof of concept, approximating the 3D case of a cell flowing in a microfluidic channel interfaced with a photonic chip. The far field intensity of the light exiting the scatterers cluster is then collected by an array of virtual pixels that approximately simulate a line scan image sensor. The pixels outputs are fed into a linear classifier that can be implemented in the electric domain.

Both a cell in a microfluidic channel and the proposed silica scatterers were modeled in the same 2D FDTD simulation (FIG. 5) employing Lumerical's FDTD Solutions software. A monochromatic plane wave (vacuum wavelength $\lambda=532$ nm) of constant intensity impinges transversely on a microfluidic channel (15 µm wide) filled with water. The channel interfaces with a region containing layers of elliptic scatterers (0.5 µm wide and 1 µm long) made of SiO2 embedded in $Si_3N_4$. At the end of the scatterers region, a vertical far field monitor covers the total length of the simulated space. The simulation region is 28 µm long along the vertical direction and from 20 µm to 30 µm along the horizontal direction, depending on the number of scatterers layers. The mesh size is $\lambda/13$.

It should be stressed that the scope of this work is to provide a proof-of-concept of a new approach to photonics machine learning, that can be generalized to many other implementations besides the cell classification based on the nucleus size. Therefore, the dimensionality of the simulation, the structures dimensions and the cell model are the consequence of a trade-off between closeness to reality, saving of computational time and the search of a sufficiently complex (but not overly so) task. In any case, all the simulated objects a part from the scatterers were designed independently of the classification results.

Cell Model

The cell model is composed by a cytoplasm region ($n_{cytoplasm}=1.37$) surrounding a nucleus region ($n_{nucleus}=1.399$). In order to have a different cell shape for each simulation, a 2D randomized cell model was employed, based on distorted ellipses. Considering the ellipse equation in polar coordinates ($\rho$ is the distance from the origin and $\theta$ the angle with respect to the horizontal axis)

$$\frac{\rho^2\cos^2\theta}{a^2} + \frac{\rho^2\sin^2\theta}{b^2} = 1$$

a surface modulation is introduced through the following substitution:

$$\rho \rightarrow \rho(1+A\cos(\omega\theta))$$

In addition, irregularities of the cell external surface are simulated by adding a noisy high-frequency modulation through:

$$\rho \rightarrow \rho + B\text{rand}_s$$

where $\text{rand}_s$ is a random number sampled from an uniform distribution from $-1$ to $+1$ for each point of the surface. The cytoplasm and the nucleus were designed using a 1000 vertices polygon, and the last substitution introduces 1000 random variables in the cell model. The other parameters are chosen as follows (subscript c stays for 'cytoplasm' and n for 'nucleus'):

$a_c=b_c=(5+0.5\text{rand})$ µm, $A_c=0.1+0.09\text{rand}$, $\omega_c=(3+2.7\text{rand})\text{rad}^{-1}$, $B_c=0.2$ for the cytoplasm and $$a_n = b_n = \begin{cases} (1.2 + 0.12 \text{ rand})\mu m & \text{'normal' cells} \\ (25 + 0.25 \text{ rand})\mu m & \text{'cancer' cells} \end{cases}$$

$A_n=0.1+0.09\text{rand}$, $\omega_n=(3+2.7\text{rand})\text{rad}^{-1}$, $B_{cn}=0$ for the nucleus.

Here rand is a random variable with uniform distribution from $-1$ to $+1$. In addition, the cytoplasm and the nucleus center displacements are given respectively by xc=yc=rand×1 µm, xn=xc+ac0.3 rand and yn=yc+bc0.3rand. Note that even if the expressions for the couples ac, bc, an, bn and xc, yc are equal, they can differ in their values being rand a random variable.

The photonic stage containing the scatterers is intended to exploit the nonlinearity of the transfer function that relates the phase shift accumulated by the light through the cell to the corresponding interference pattern measured by an image sensor. In fact, it has been proven that an arbitrary nonlinear transfer function, which is able to sufficiently separate different inputs into different outputs and that satisfies suitable stability requirements, can assist a proper (trained) linear combination in order to approximate any continuous function of the input on compact subsets of real numbers. This machine learning technique, that combines a fixed (untrained) nonlinear system with a tunable (trainable) weighted sum, is called reservoir computing (RC) when applied in the processing of time-dependent signals. The approach discussed in this example is based on the same principle but it considers a spatially distributed nonlinear stage excited by a space-dependent signal instead of a dynamical nonlinear system (called reservoir) excited by a time-dependent signal. Generally, the main advantages of RC with respect to other machine learning techniques are that only a linear readout (in this case a linear classifier) needs to be trained and that it is easily implemented in hardware. In this case, the pillar scatterers stage acts as 'spatial' reservoir and projects onto the far-field intensity a very intricate nonlinear mapping of the phase information, that can be synthesized as a linear combination of sinusoidal functions of phase-shifts differences. This parallel processing is carried out nearly instantaneously with respect to both the cell movement and the operating speed of an electronic computer, providing an important advantage over other machine learning solutions in the electric domain. It should be stressed that the phase-to-intensity nonlinearity is already expressed by the interference pattern projected by the cell alone (without scatterers). However, the complexity of such a nonlinear mapping can be enhanced and controlled by the use of scatterers in order to increase the performance of a subsequent linear classification, i.e. looking for the 'edge of chaos'. The exploitation of light interference in order to fabricate a passive integrated wave-based computing system using linear optical media was demonstrated, but the time dependent input information was encoded in the intensity of a laser signal and therefore the transfer function to the output detector was quadratic (amplitude to intensity). Here, being the input information encoded in the phase of a laser signal, the readout transfer function can be, for instance, sinusoidal with respect to that input. The sine, for example, can be profitably employed as activation function in feedforward neural networks under suitable conditions.

According to embodiments of the present invention following machine learning aspects may be implemented, in the present example. The far-field intensity profile obtained is divided in Npix bins (or pixels) and the integration over each bin is fed into a logistic regression. The Scikit-learn Python library was employed, using the 'liblinear' solver. For each tested scatterer configuration a number Nsamp of simulations was performed randomly varying the cell shape, as described in the previous section. In half of the Nsamp simulations a normal cell was considered, while in the remaining half a cancer cell (with bigger nucleus) was used. 75% of these two sets was employed in the training of the logistic regression, while the rest was used as test.

A Gaussian white noise was added a posteriori on the interference patterns before they were divided in bins. The noise standard deviation is chosen to be 1% of the maximum intensity over the sample set.

A study on the dependency of the classification3 test error on the regularization (L1 and L2) strength and on $N_{samp}$ was carried out on the two cases with and without the use of scatterers, on a set of 2000 samples each. For this investigation, a 4 layer scatterer configuration 4 was considered, with $A_{rand}$=150 nm and D=1.846 µm. The study pointed out that regularization had no significant positive effect on the performances of the two classification tasks. Furthermore, it showed that the learning curve (test error v.s. number of samples) converged around $N_{samp}$=800 when the scatterers were used. This value for $N_{samp}$ and no regularization were the conditions employed for the investigation on the scatterer configuration discussed in the next session. The classification dependency on the number of pixels and training epochs was instead kept under direct control by performing sweeps for each tested configuration.

Figure 11A:
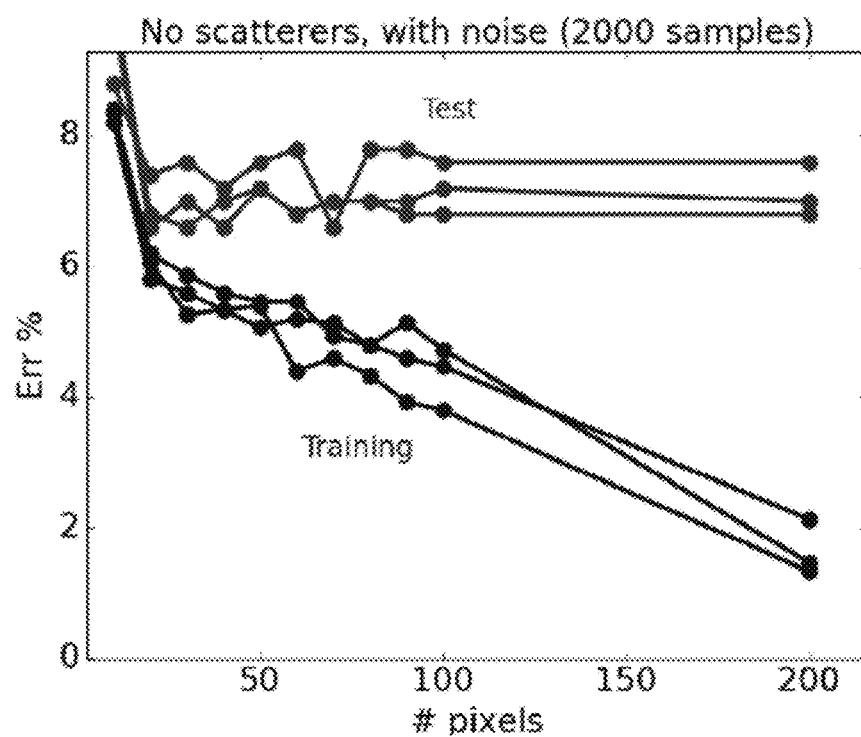
FIG. 11a and FIG. 11b illustrate test and training errors of the classification without scatterers and with added noise (FIG. 11a) and with 4 layers of scatterers and with added noise (FIG. 11b), illustrating features of embodiments of the present invention.
Figure 11B:
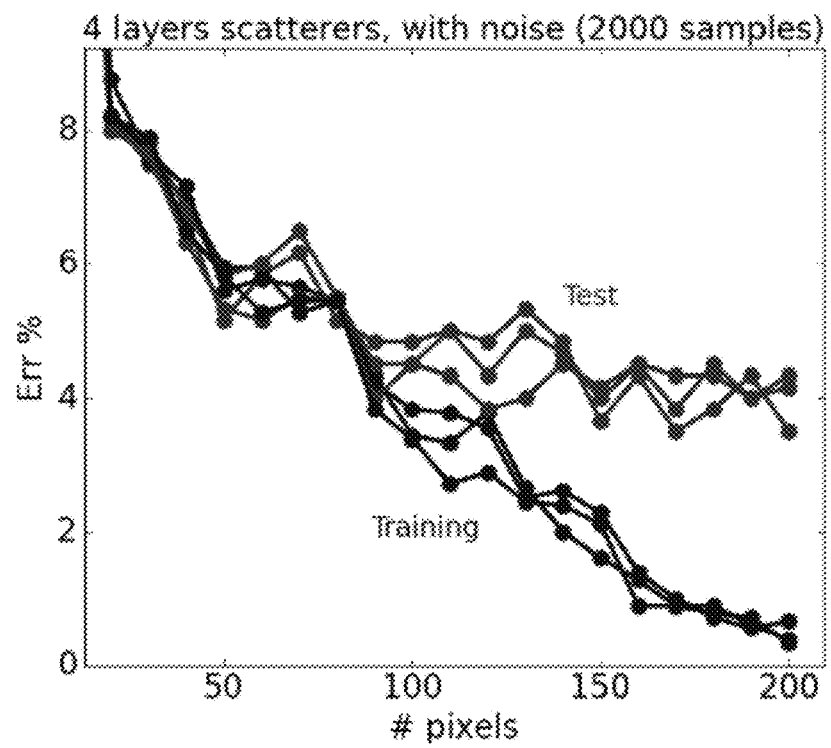
Figure 12A:
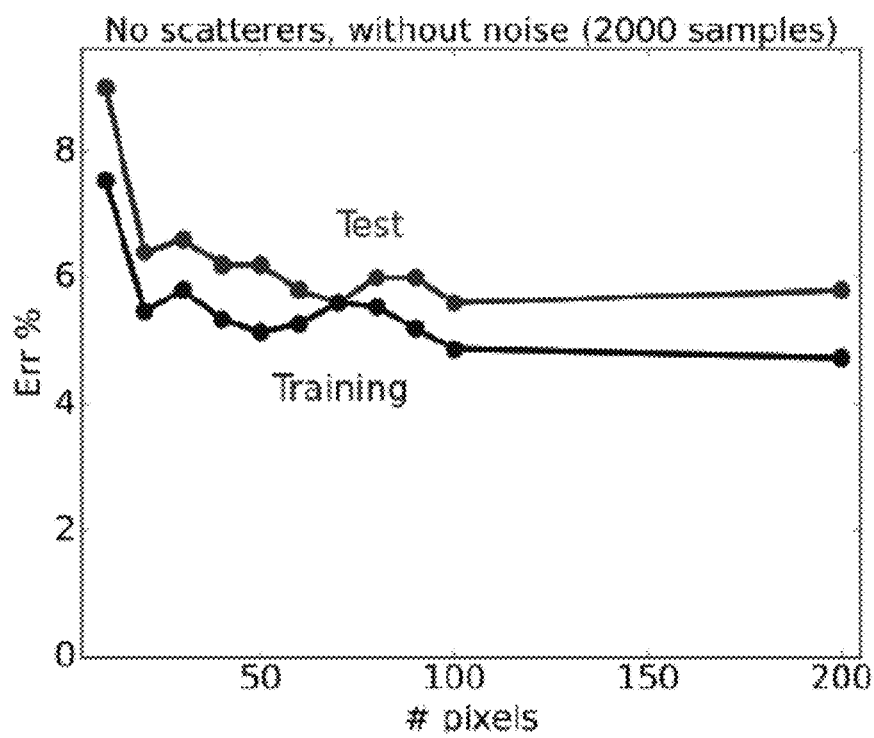
FIG. 12a and FIG. 12b illustrate test and training errors of the classification without scatterers and without added noise (FIG. 12a) and with 4 layers of scatterers and without added noise (FIG. 12b), illustrating features of embodiments of the present invention.
Figure 12B:
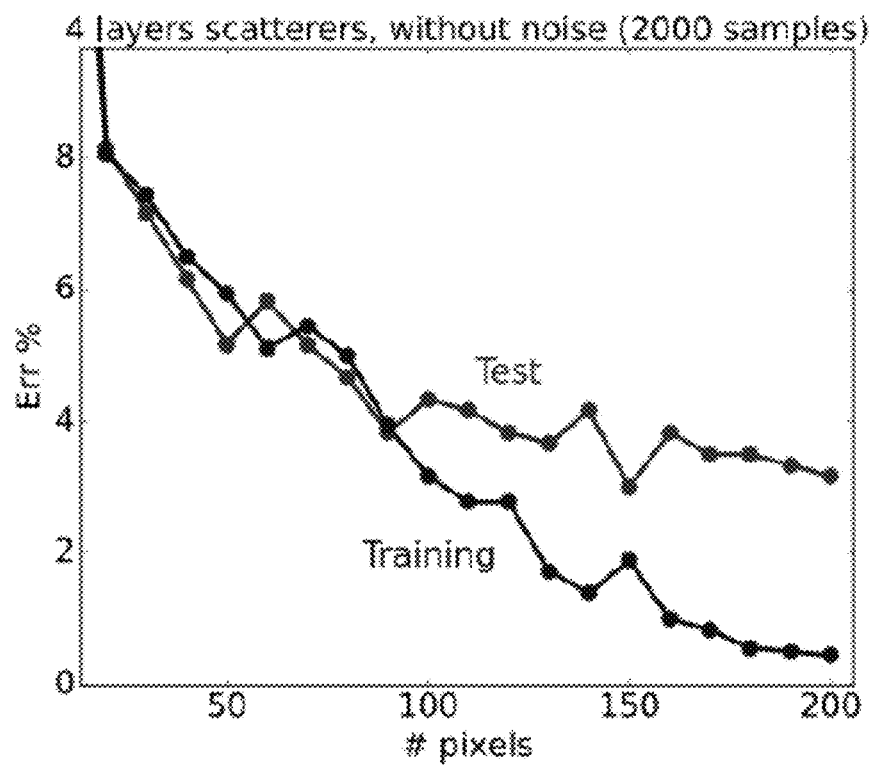
Figure 13:
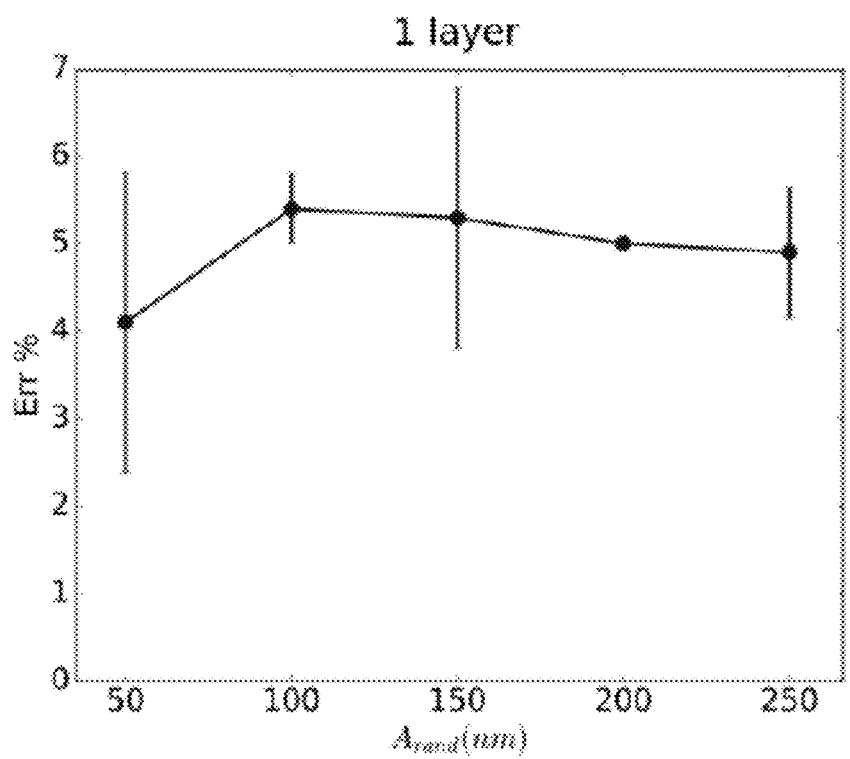
FIG. 13 to FIG. 17 illustrate test errors as function of the random displacement amplitude of the silica scatters for respectively a 1, 2, 3, 4 or 5 layer configuration, according to embodiments of the present invention.
Figure 14:
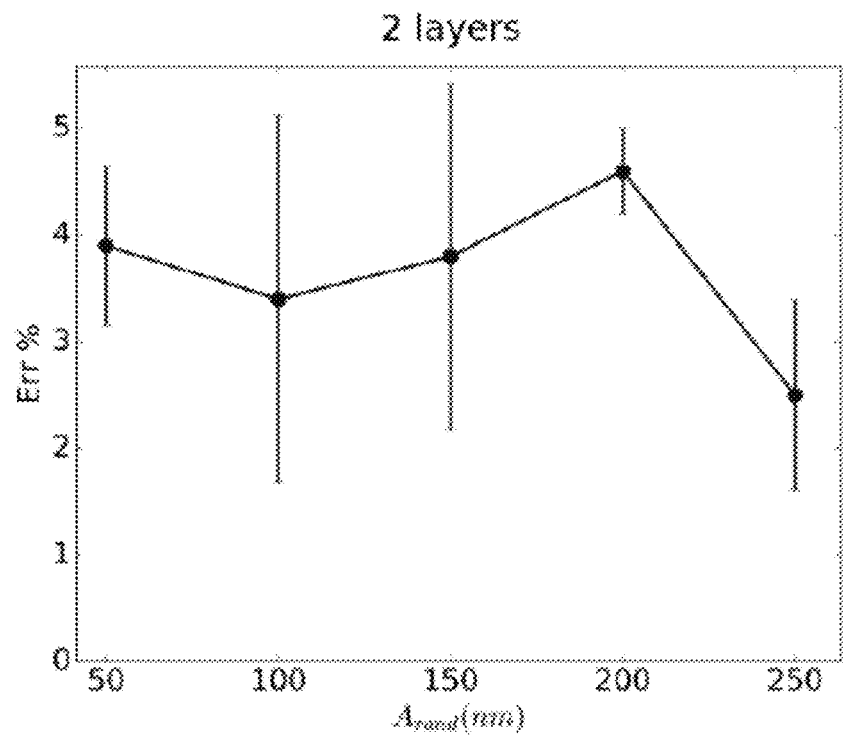
Figure 15:
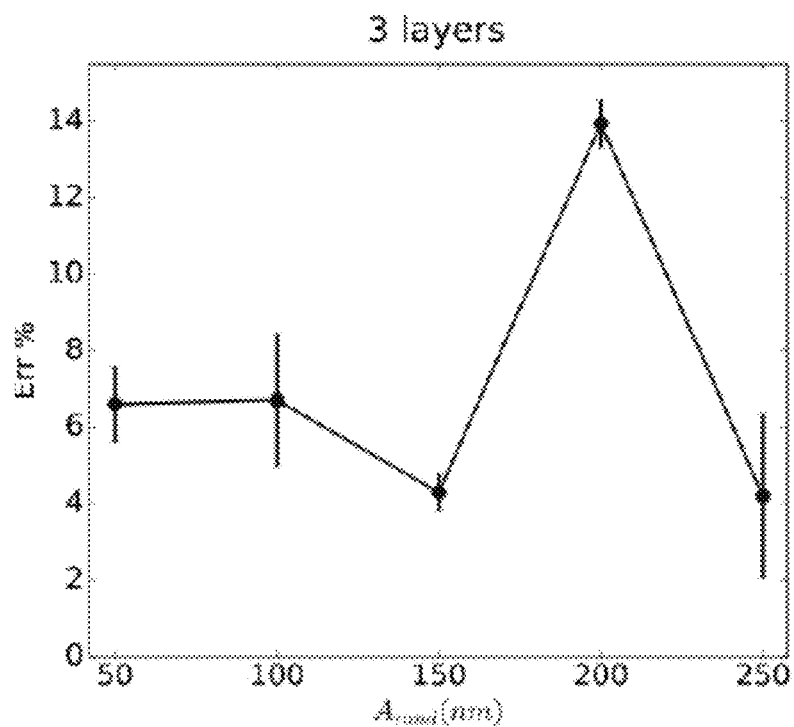
Figure 16:
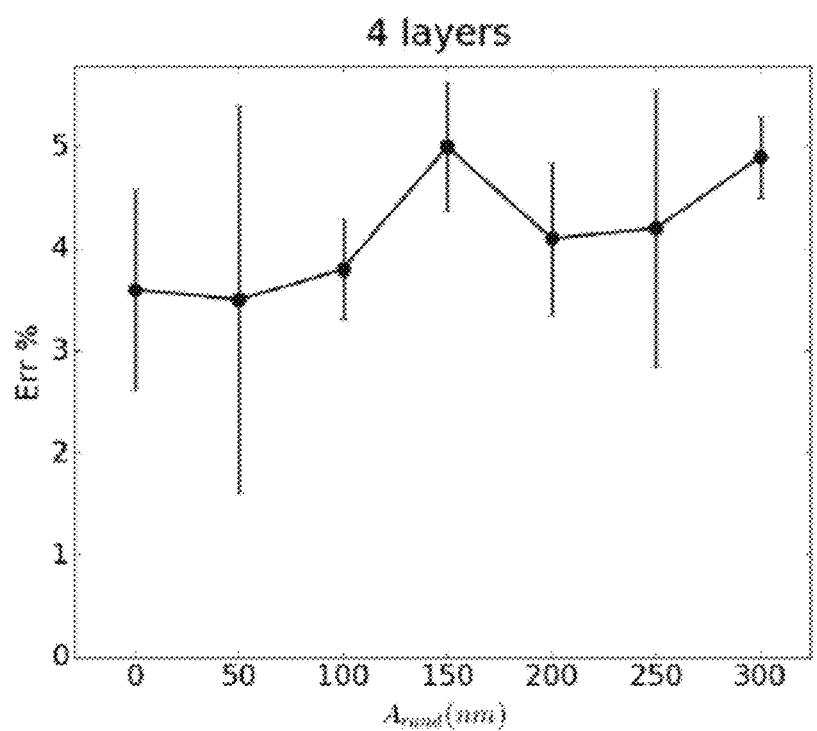
Figure 17:
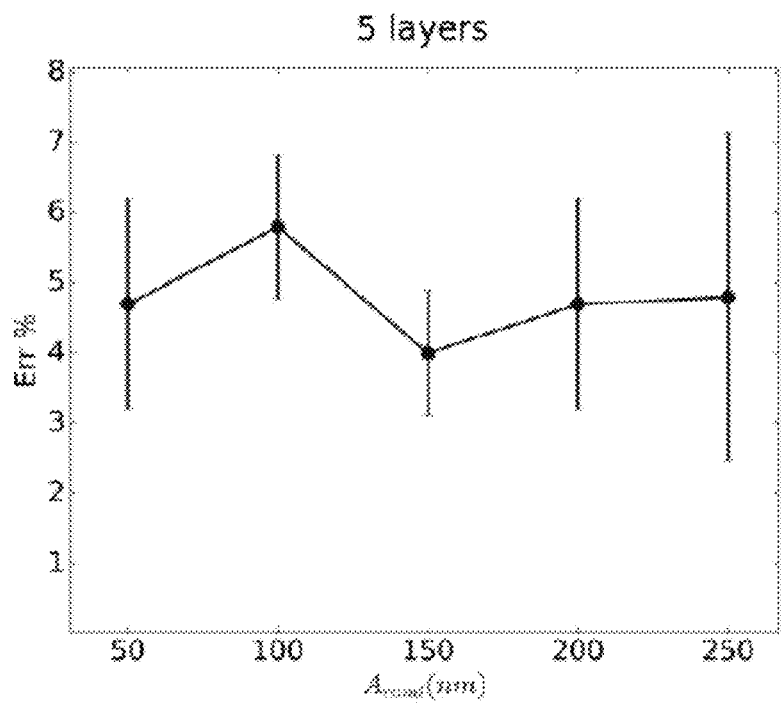

A first comparison is done between the classification error on the test samples when no scatterers are present (FIGS. 11a and 12a) and when 4 layers with $A_{rand}$=150 nm and D=1.846 µm are employed (FIGS. 11b and 12b). In the first case, the angle range for which the far-field intensity is not negligible is between −6° and 6° (FIG. 6a) and this is the range to which the number of pixels refers. In the second case, instead, the chosen angle range is between −60° and 60° (FIG. 6c). This implies that, at equal number of pixels, the acquisition of the hologram of the cell alone has a resolution ten times finer than the hologram acquisition performed when the scatterers are present. This explains the jumps in FIGS. 11a and 12a between the point at 100 pixels and the point at 200 pixels: the output resolution of the FDTD simulation was reached. Each point drawn in these graphs corresponds to an optimal choice of number of epochs.

It can noted that in every case the classification assisted with the scatterers layers shows a smaller error provided that a sufficient number of pixels is used (>=50).

An exploration of the impact of the scatterer configuration on the classification error was made by considering the possible combinations (simulating 800 samples each) of $N_{layers}$=1, 2, 3, 4, 5 and $A_{rand}$=50, 100, 150, 200, 250 nanometers, keeping D=1.846 µm fixed. In order to represent the results in a compact way, only the minimum test error found varying the number of training epochs and the number of pixels (from 10 to 200) is plotted (FIGS. 13, 14, 15, 16 and 17) for each configuration. The error bars correspond to a confidence interval of 95% computed on 5 repetitions of the training and test phases of the logistic regression. The variability is introduced by the added white noise. The displayed error bars are large due to the use of a limited number of training samples. Although there appear to be some weakly pronounced optima (e.g. at 2 layers for $A_{rand}$=250) these are probably not significant because of the limited number of training samples and the fact that we use a 2D model as opposed to a 3D model.

A similar investigation was performed changing the noise level and for other two values of the distance D between the layers, that are D=2.85 µm and D=3.40 µm. These two distances are respectively the first maximum and minimum point of the far-field transmission as a function of D, considering four layers of scatterers without any random displacement. These configurations did not showed any significant improved performance as either. So, the main conclusion of these preliminary geometrical optimisations are that although the presence of the scatterers itself has a significant effect compared to the case without scatterers, there exact geometrical parameters seem to be less important. This means that any given scatterer configuration will probably show good performance on other tasks as well.

Under the oversimplifying assumption that the refractive index structure of the cell does not significantly change the spatial propagation of light, the whole phase to intensity transfer function can be essentially written as a weighted sum of the sine and the cosine of every possible phase difference Δθ between the optical paths through the cell. Thus, in the attempt of recognizing the difference between cells with small and big nucleus, the logistic regression needs to be sensitive towards intensity variations ΔI similar to the following:

$$\Delta I \sim C_1[\sin(\Delta\theta_{cn}) - \sin(\Delta\theta_{nn})] + C_2[\cos(\Delta\theta_{cn}) - \cos(\Delta\theta_{nn})]$$

$$\text{With } \Delta\theta_{cn} = \frac{2\pi D_{cancer}}{\lambda}(n_{nucleus} - n_{cytoplasm})$$

$$\Delta\theta_{nn} = \frac{2\pi D_{normal}}{\lambda}(n_{nucleus} - n_{cytoplasm})$$

where $C_1$ and $C_2$ are constants, $\Delta\theta_{cn}$ and $\Delta\theta_{nn}$ are estimates of the phase shift produced by the nucleus of a 'cancer' cell (with average diameter $D_{cancer}$~2.5 µm) and a 'normal' cell (with average diameter $D_{normal}$~1.2 µm) respectively. $\lambda$=0.532 µm is the wavelength of the considered radiation, $n_{nucleus}$=1.39 and $n_{cytoplasm}$=1.37 are the refractive index of the nucleus and of the cytoplasm in the employed cell model. In order to exploit the nonlinearity of the sinusoidal function for the classification task, the difference $\Delta\theta_{cn}-\Delta\theta_{nn}$ should be not too small and not too big with respect to $\pi$. Under the considered conditions, $\Delta\theta_{cn}-\Delta\theta_{nn}$~0.3, which is quite small.

Figure 18A:
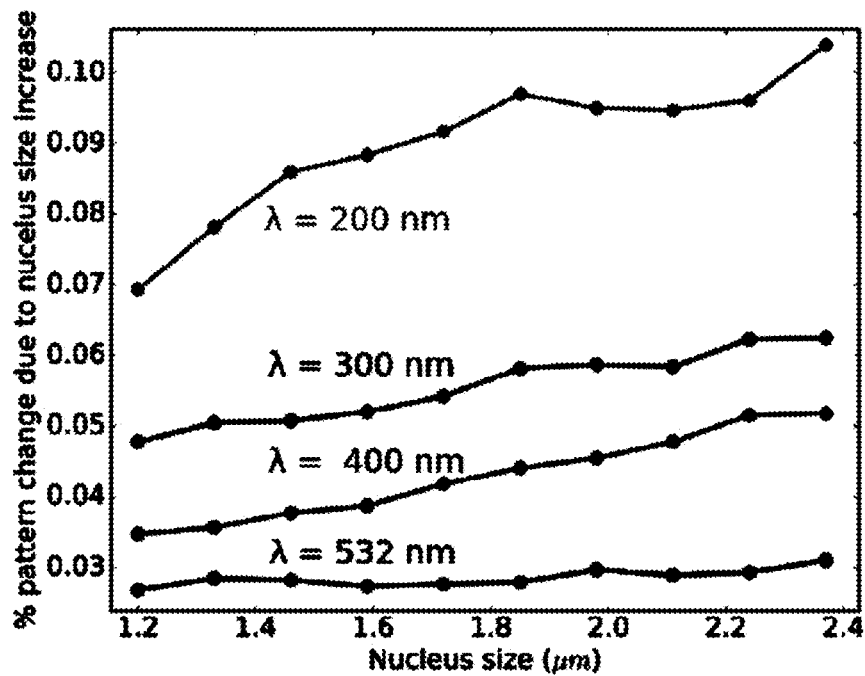
FIGS. 18a and 18b illustrate the change in the acquired hologram due to small increases of the nucleus size for different wavelengths (FIG. 18a) as well as optical losses on the collected far-field intensity due to the scatterers presence as function of cell nucleus size for different wavelengths (FIG. 18b) illustrating features of embodiments of the present invention.
Figure 18B:
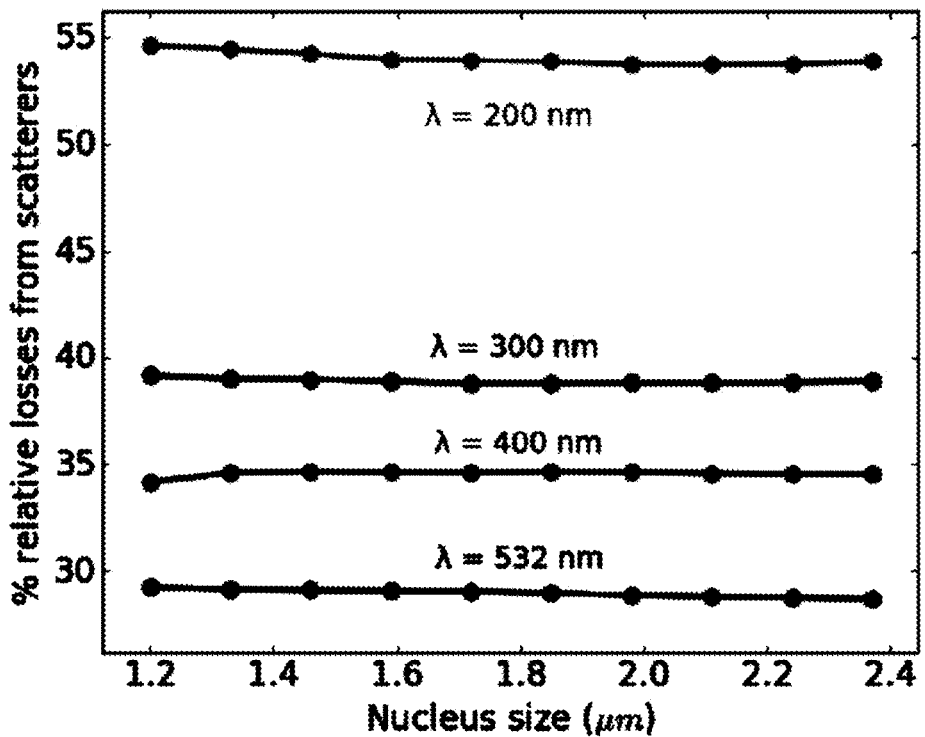
Figure 19A:
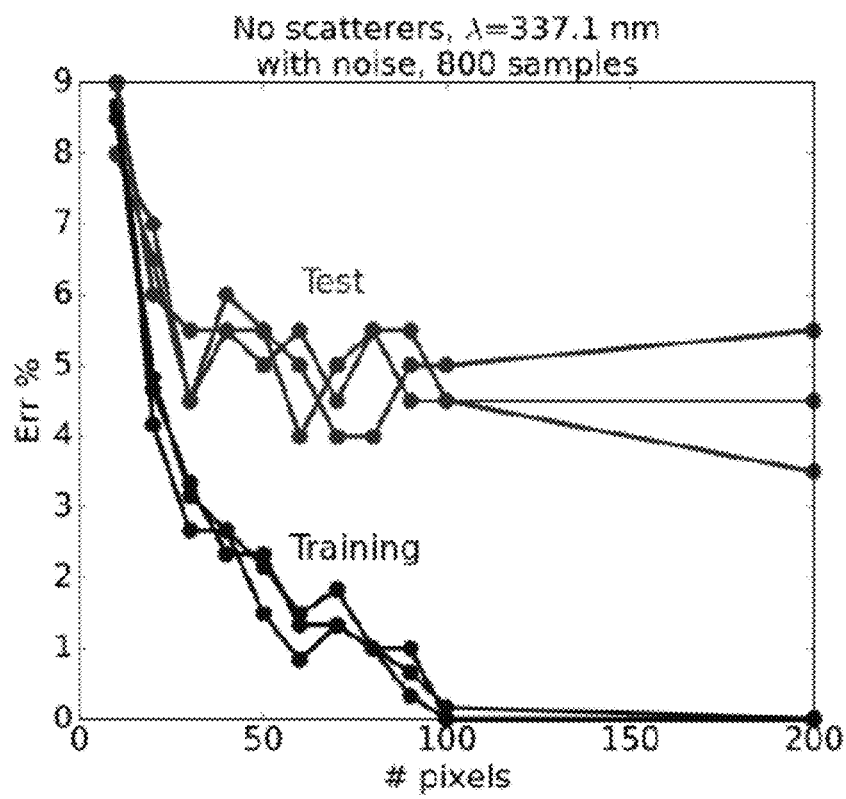
FIG. 19a and FIG. 19b illustrate test and training errors of the classification without scatterers and with added noise (FIG. 19a) and with 4 layers of scatterers and with added noise (FIG. 19b), for wavelength 337.1 nm illustrating features of embodiments of the present invention.
Figure 19B:
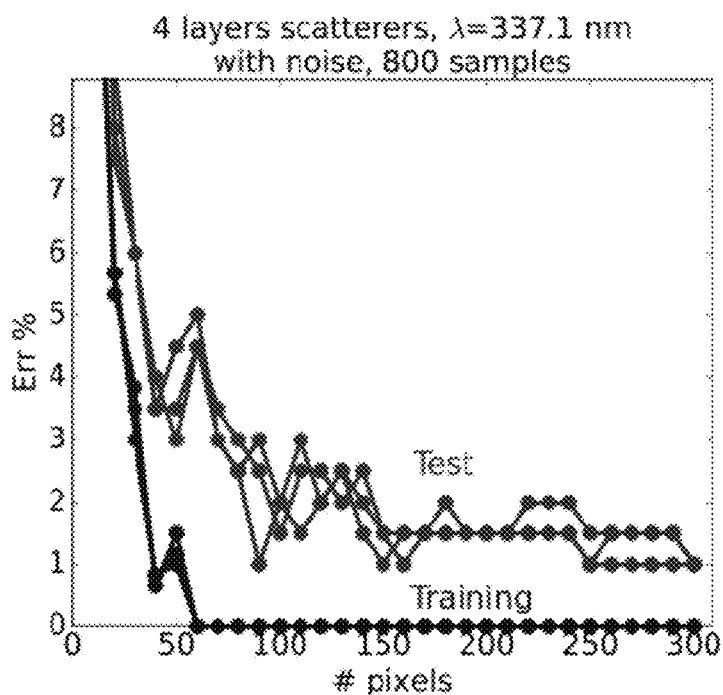
Figure 20A:
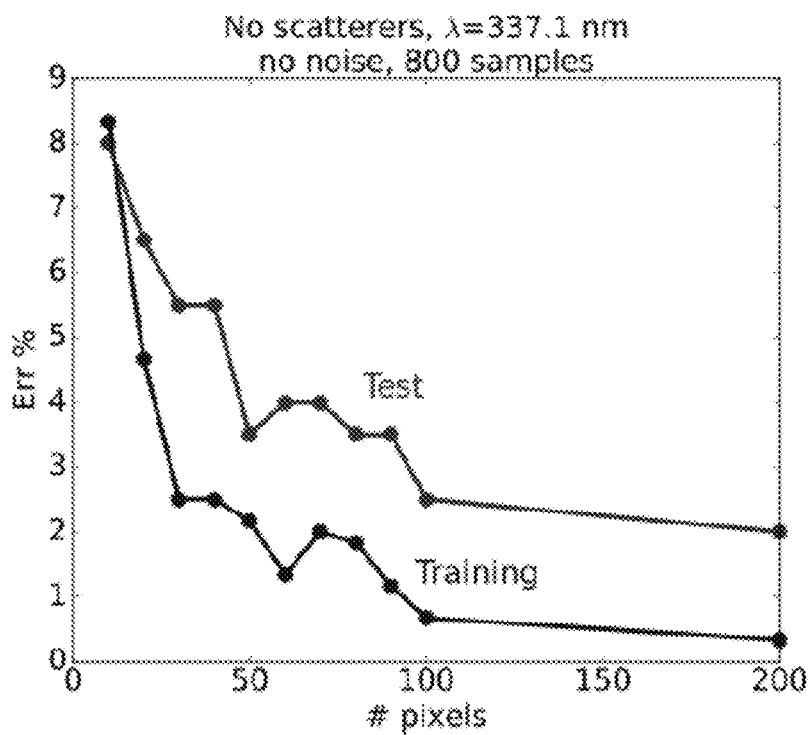
FIG. 20a and FIG. 20b illustrate test and training errors of the classification without scatterers and without added noise (FIG. 20a) and with 4 layers of scatterers and without added noise (FIG. 20b), for wavelength 337.1 nm illustrating features of embodiments of the present invention.
Figure 20B:
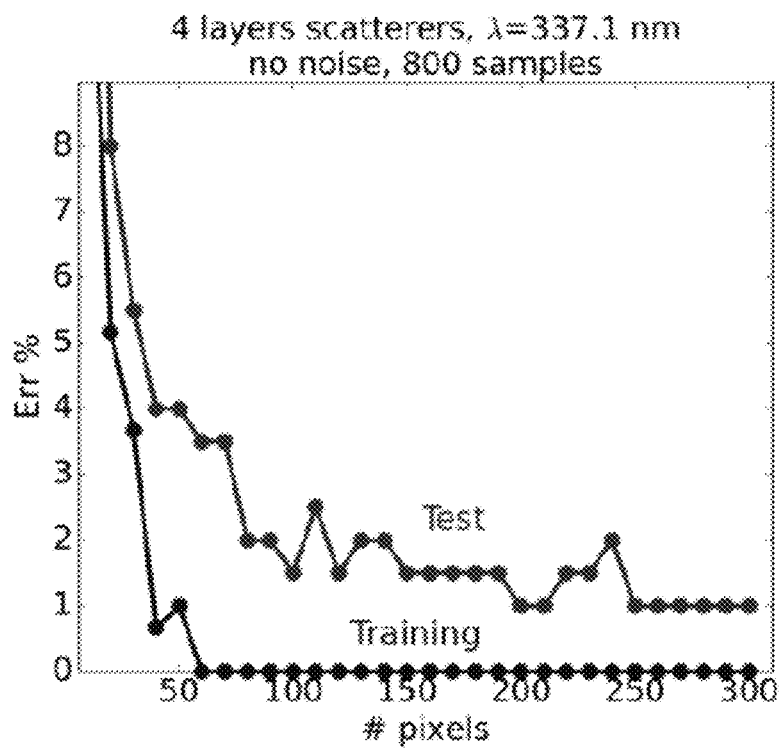

There are at least two ways to make this value bigger: lowering the wavelength or increasing the number of times the light passes through the cell by employing an optical cavity (e.g. a Fabry-Perot resonator). In this example, the first option was evaluated. Considering the wavelengths $\lambda$=532, 400, 300 and 200 nm, the overall change in the acquired hologram was calculated for small modifications (of 130 nm) of the nucleus size (FIG. 10a), keeping the rest of the simulation parameters fixed. The dispersion of the employed materials was accounted for and, in particular, the same absolute contrast was kept between the refractive indexes in the cell model and the water. As expected, the impact of such modifications on the acquired interference pattern increases significantly by decreasing the laser wavelength. On the other hand, the same happens to the transmission losses due to the presence of the scatterers (FIG. 18b).

In order to consider a plausible UV laser source, the classification performance was investigated (FIGS. 19a,19b, 20a and 20b) using $\lambda$=337.1 nm, without scatterers and employing 4 layers of scatterers with $A_{rand}$=150 nm, D=2.85 µm. The overall classification error is significantly lower with respect to the previous cases using $\lambda$=532 nm and, as before, the use of scatterers has a positive impact on the performance. In particular, as expected from a reservoir-like approach, the presence of the scatterer layers seems to considerably increase the noise robustness of the classification task.

The invention claimed is:

1. An object classification system for classifying objects, the object classification system comprising:
    an imaging region adapted for irradiating an object of interest,
    an arrayed detector,
    a mixing unit configured for mixing the irradiation stemming from the object of interest by reflecting or scattering on average at least three times the irradiation after its interaction with the object of interest and prior to said detection.

2. The object classification system according to claim 1, wherein the system further comprises a classifier for classifying the objects based on the irradiation obtained after said mixing.

3. The object classification system according to claim 2, wherein the classifier is a linear classifier.

4. The object classification system according to claim 3, wherein the arrayed detector is a line scan image sensor and wherein the linear classifier is implemented in the electrical field, receiving input signals from the line scan image sensor.

5. The object classification system according to claim 4, wherein the classifier is based on a weighted sum of the input signals.

6. The object classification system according to claim 1, wherein the arrayed detector is a line scan image sensor.

7. The object classification system according to claim 1, wherein the mixing unit comprises a random set of scattering objects.

8. The object classification system according to claim 7, wherein the scattering objects are scattering pillars.

9. The object classification system according to claim 1, wherein the random set of scattering objects are positioned in a cavity.

10. The object classification system according to claim 9, the cavity being formed from silicon nitride and the scattering pillars being made of silica.

11. The object classification system according to claim 1, wherein the mixing unit is a photonic crystal cavity or
    wherein the mixing unit is a cavity made in silicon, whereby ferroelectric thin films are coated on the cavity.

12. The object classification system according to claim 1, wherein the mixing unit is a photonic crystal cavity made of silicon rods wherein in the middle nonlinear polymers are introduced.

13. The object classification system according to claim 1, wherein the cavity is made in a III-V material.

14. The object classification system according to claim 1, the system comprising a plurality of mixing units coupled in a hierarchical arrangement.

15. The object classification system according to claim 14, wherein the mixing units being coupled in a hierarchical arrangement comprises a first mixing unit taking care of lower-level features in the input signal and further mixing units for taking care of higher-level features.

16. The object classification system according to claim 1, wherein the imaging region adapted for irradiating an object of interest comprises a microfluidic channel for carrying the object in a fluid.

17. The object classification system according to claim 1, wherein the system is a cell classification system.

18. Use of an object classification system according to claim 1 for classifying cells.

19. A method for classifying objects, the method comprising:
    irradiating an object of interest
    mixing the irradiation after interacting with the object of interest by reflecting or scattering at least three times using a mixing unit,
    detecting the mixed irradiation with an arrayed detector.

20. A method according to claim 19, wherein the mixing comprises mixing a static, non-time dependent irradiation signal, detecting said mixed signal and deriving therefrom a classification for the object of interest, or
    wherein the method comprises applying a classification of the detected mixed irradiation.

* * * * *